United States Patent
Cloos

(10) Patent No.: US 10,670,682 B2
(45) Date of Patent: Jun. 2, 2020

(54) PARALLEL TRANSMISSION BY SPIN DYNAMIC FINGERPRINTING

(71) Applicant: New York University, New York, NY (US)

(72) Inventor: Martijn Anton Hendrik Cloos, New York, NY (US)

(73) Assignee: NEW YORK UNIVERSITY, New York, NY (US)

(*) Notice: Subject to any disclaimer, the term of this patent is extended or adjusted under 35 U.S.C. 154(b) by 501 days.

(21) Appl. No.: 15/036,667

(22) PCT Filed: Nov. 14, 2014

(86) PCT No.: PCT/US2014/065803
§ 371 (c)(1),
(2) Date: May 13, 2016

(87) PCT Pub. No.: WO2015/073894
PCT Pub. Date: May 21, 2015

(65) Prior Publication Data
US 2016/0282436 A1   Sep. 29, 2016

Related U.S. Application Data

(60) Provisional application No. 61/904,716, filed on Nov. 15, 2013.

(51) Int. Cl.
*G01R 31/00* (2006.01)
*G01R 33/561* (2006.01)
(Continued)

(52) U.S. Cl.
CPC .......... *G01R 33/5612* (2013.01); *A61B 5/055* (2013.01); *G01R 33/246* (2013.01);
(Continued)

(58) Field of Classification Search
USPC ................................ 324/309, 310, 312–317
See application file for complete search history.

(56) References Cited

U.S. PATENT DOCUMENTS 7,218,112 B2   5/2007  Ladebeck et al.
8,299,789 B2   10/2012 Heid et al.
(Continued)

FOREIGN PATENT DOCUMENTS

WO   WO-2015/073894 A2   5/2015

OTHER PUBLICATIONS

Chen, Y., et al., "Magnetic resonance fingerprinting (MRF) for rapid quantitative abdominal imaging", Proc. Intl. Soc. Mag. Reson. Med., 2014, 22:0561.
(Continued)

*Primary Examiner* — Vincent Q Nguyen
(74) *Attorney, Agent, or Firm* — Foley & Lardner LLP

(57) ABSTRACT

A general framework is for signal encoding in MRF that enables simultaneous transmit and receive encoding to accelerate the acquisition process, or improve the fidelity of the final image/parameter-map per unit scan time. The proposed method and systems capitalize on the distinct spatial variations in the sensitivity profile of each transmit-coil to reduce the acquisition time, and/or improve the fidelity of the final parameter-map per unit time.

20 Claims, 17 Drawing Sheets

(51) Int. Cl.
    A61B 5/055    (2006.01)
    G01R 33/24    (2006.01)
    G01R 33/48    (2006.01)
    G01R 33/483   (2006.01)
    G01R 33/565   (2006.01)
    G01R 33/50    (2006.01)
    G01R 33/56    (2006.01)

(52) U.S. Cl.
    CPC ..... *G01R 33/4828* (2013.01); *G01R 33/4835* (2013.01); *G01R 33/56545* (2013.01); *G01R 33/50* (2013.01); *G01R 33/5602* (2013.01); *G01R 33/5608* (2013.01)

(56) References Cited

U.S. PATENT DOCUMENTS

| | | | |
|---|---|---|---|
| 8,405,395 | B2 | 3/2013 | Setsompop et al. |
| 8,680,861 | B1 | 3/2014 | Morrone |
| 9,897,675 | B2 | 2/2018 | Setsompop et al. |
| 2002/0069242 | A1 | 6/2002 | Berns |
| 2005/0141757 | A1* | 6/2005 | Ayache ............... G06T 7/0012 382/128 |
| 2008/0150532 | A1 | 6/2008 | Slavin et al. |
| 2010/0090694 | A1 | 4/2010 | Heid et al. |
| 2010/0259263 | A1 | 10/2010 | Holland et al. |
| 2012/0235678 | A1 | 9/2012 | Seiberlich et al. |
| 2012/0256626 | A1* | 10/2012 | Adalsteinsson .... G01R 33/5612 324/309 |
| 2013/0038326 | A1 | 2/2013 | Amadon et al. |
| 2013/0271135 | A1* | 10/2013 | Ozen ................... G01R 33/543 324/309 |
| 2014/0253126 | A1* | 9/2014 | Habara ............. G01R 33/3415 324/322 |
| 2015/0002150 | A1* | 1/2015 | Weissler ............... A61B 6/037 324/309 |
| 2015/0300963 | A1 | 10/2015 | Haidekker et al. |
| 2015/0301141 | A1 | 10/2015 | Griswold et al. |
| 2015/0346300 | A1 | 12/2015 | Setsompop et al. |
| 2016/0116559 | A1 | 4/2016 | Cohen |
| 2016/0282436 | A1 | 9/2016 | Cloos |
| 2016/0291105 | A1 | 10/2016 | Knoll et al. |
| 2016/0291107 | A1 | 10/2016 | Rosen et al. |
| 2019/0033414 | A1 | 1/2019 | Sofka et al. |
| 2019/0033415 | A1 | 1/2019 | Sofka et al. |

OTHER PUBLICATIONS

Cloos, M. A., et al., "Plug and Play Parallel Transmission at 7 and 9.4 Tesla based on Principles from MR Fingerprinting", Proc. Intl. Soc. Mag. Reson. Med., 2014, 22:0542.

Doneva, M., et al., "Compressed Sensing Reconstruction for Magnetic Resonance Parameter Mapping", Magnetic Resonance in Medicine, 2010, 64:1114-1120.

Ma, D., et al., "Magnetic resonance fingerprinting", Nature, Mar. 14, 2013, 495:187-193.

Extended European Search Report in EP 14861500.8, dated Jan. 22, 2018, 17 pages.

Graesslin, I., et al., "Whole Body 3T MRI System with Eight Parallel RF Transmission Channels", Proceedings of the International Society for Magnetic Resonance in Medicine, Apr. 22, 2006, 14:129.

Graesslin, I., et al., "Fully Integrated Whole Body 3T MRI System for Parallel RF Transmission", Proceedings of the International Society for Magnetic Resonance in Medicine, May 5, 2007, 15:1007.

Katscher, U., et al., "Parallel RF transmission in MRI", NMR in Biomedicine, Jan. 1, 2006, 19(3):393-400.

Nelles, M., et al., "Dual-Source Parallel RF Transmission for Clinical MR Imaging of the Spine at 3.0 T: Intraindividual Comparison with Conventional Single-Source Transmission", Radiology, Dec. 1, 2010, 257(3):743-753.

Orzada, S., et al., "Design and comparison of two eight-channel transmit/receive radiofrequency arrays for in vivo rodent imaging on a 7 T human whole-body MRI system", Medical Physics, May 2010, 37(5):2225-2232.

Weber, E., et al., "A Novel 8-Channel Transceive Volume-Array for a 9.4T Animal Scanner", Proceedings of the International Society for Magnetic Resonance in Medicine, Apr. 19, 2008, 16:151.

Partial supplementary European search report in EP 14861500.8, dated Sep. 5, 2017, 18 pages.

International Search Report and Written Opinion for Application PCT/US2014/065803, dated Feb. 13, 2015, 8 pages.

Ben-Eliezer, et al., "A New Model-Based Technique for Accurate Reconstruction of T2 Relaxation Maps from Fast Spin-Echo Data," Proceedings of the International Society for Magnetic Resonance in Medicine 21, p. 2453 (2013).

Katscher, et al., "RF encoding using a multielement parallel transmit system," Magnetic Resonance in Medicine 63(6), pp. 1463-1470 (2010).

Knoll, et al., "Simultaneous MR-PET Reconstruction Using Multi Sensor Compressed Sensing and Joint Sparsity," Proceedings of the International Society for Magnetic Resonance in Medicine 22, p. 0082 (2014).

Kosters, et al., "EMRECON: An expectation maximization based image reconstruction framework for emission tomography data," 2011 IEEE Nuclear Science Symposium Conference Record, pp. 4365-4368 (2011).

Mueller, et al., "The Alzheimer's Disease Neuroimaging Initiative," Neuroimaging Clinics of North America 15(4), pp. 869-877 (2005).

Quick, "Integrated PET/MR," Journal of Magnetic Resonance Imaging 39(2), pp. 243-258 (2014).

Ye, et al., "Accelerating Magnetic Resonance Fingerprinting (MRF) Using t-Blipped Simultaneous Multislice (SMS) Acquisition", Magnetic Resonance in Medicine 75(5), pp. 2078-2085 (2016).

\* cited by examiner

Figure 7C
Figure 7D
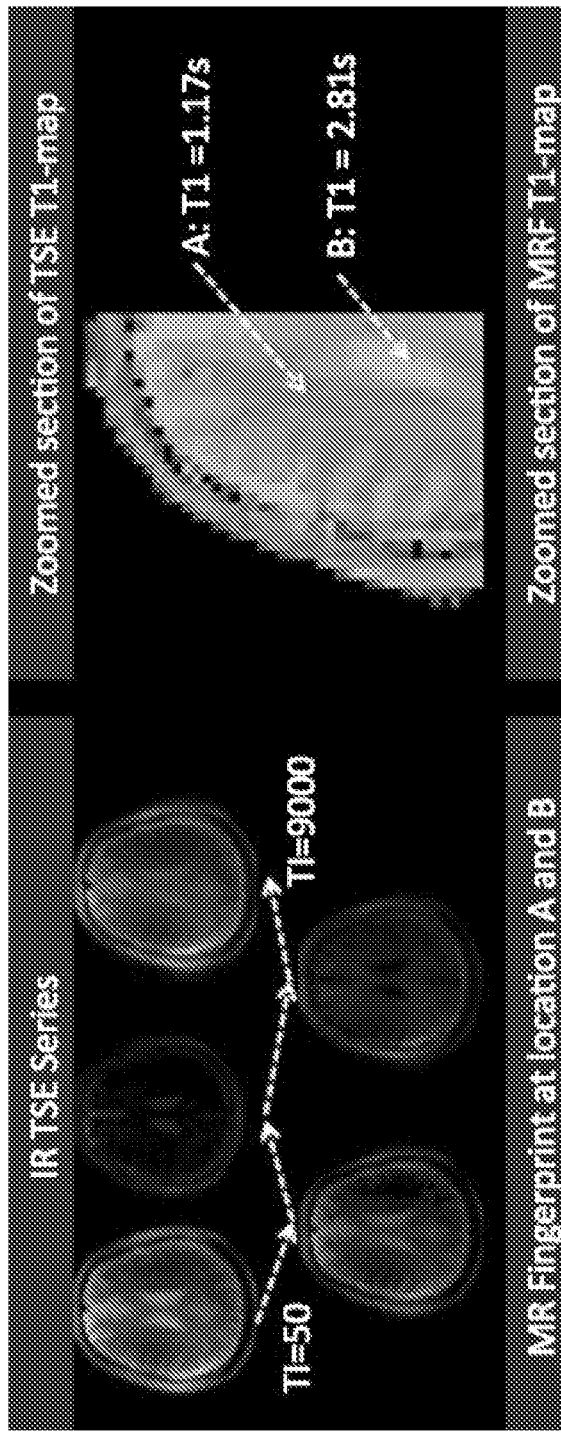
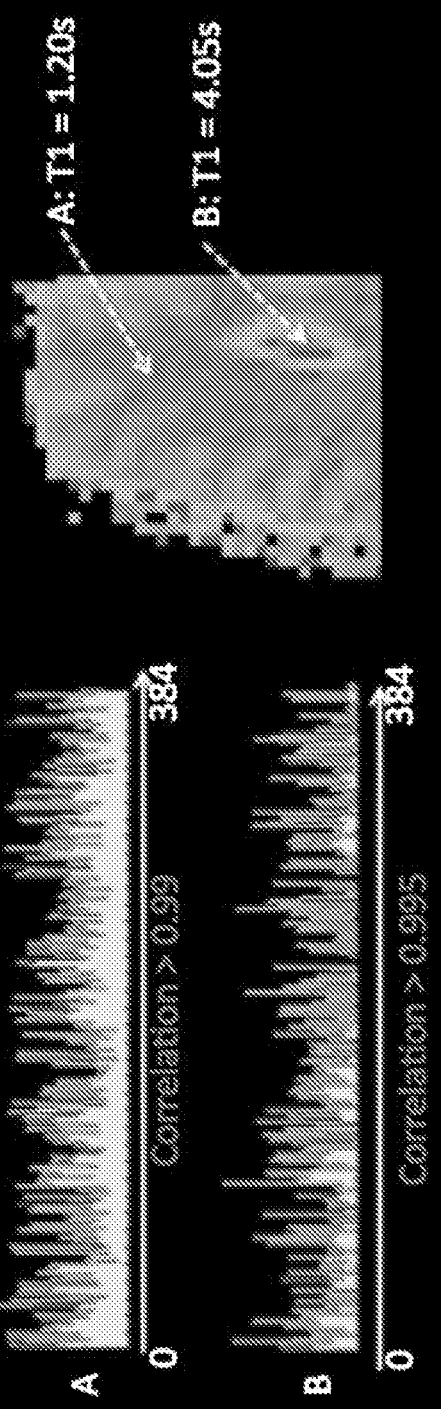
Figure 7A
Figure 7B

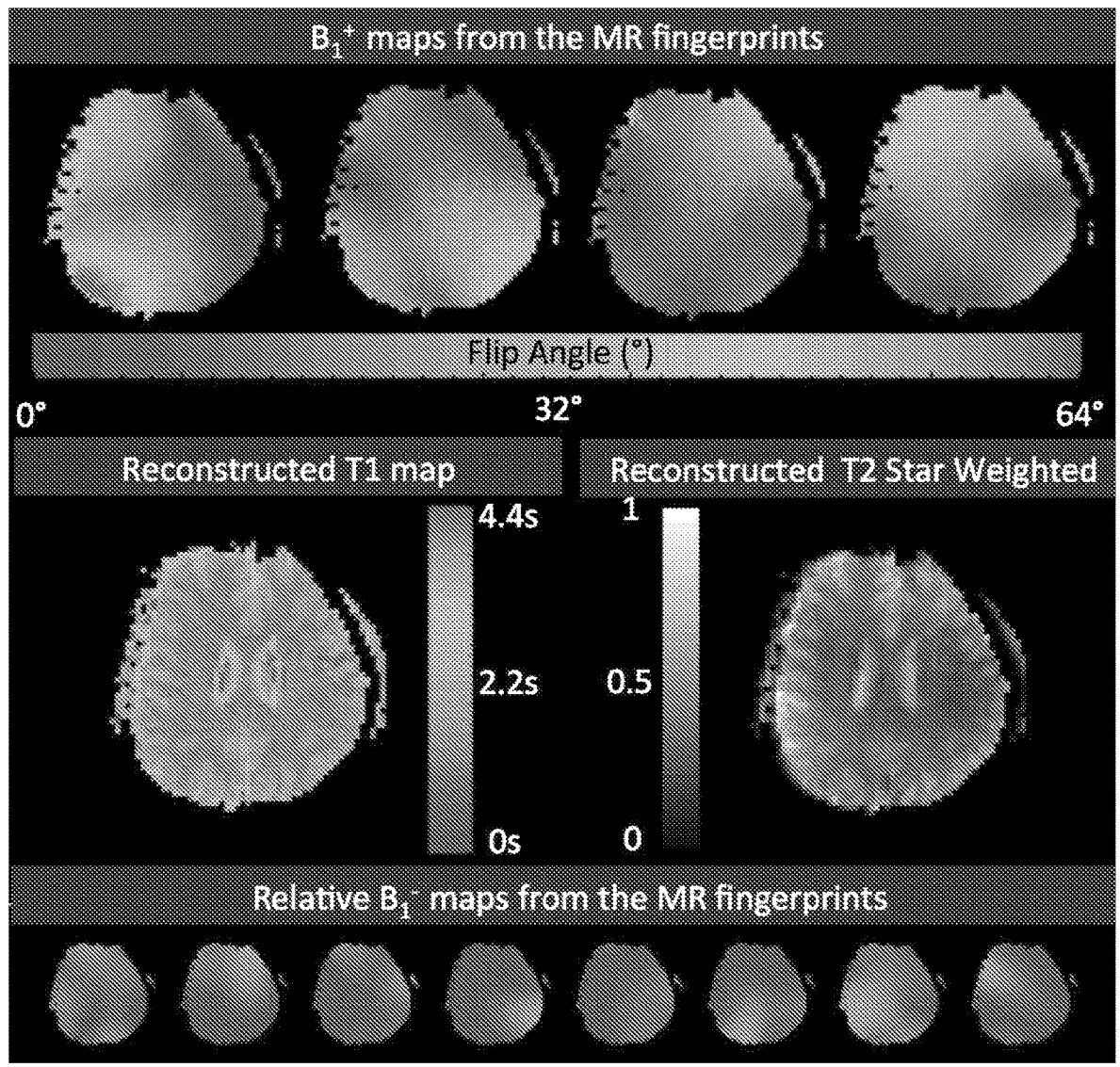
Figures 8A (top), 8B (middle, left), 8C (middle, right), and 8D (bottom)

PARALLEL TRANSMISSION BY SPIN DYNAMIC FINGERPRINTING

CROSS-REFERENCE TO RELATED APPLICATIONS

This application is a National Stage of International Application No. PCT/US2014/065803, filed Nov. 14, 2014, which claims priority to U.S. Provisional Application No. 61/904,716, filed Nov. 15, 2013, entitled SELF-CALIBRATING PARALLEL TRANSMISSION BY SPIN DYNAMIC FINGERPRINTING, reference of which are hereby incorporated in their entirety.

GOVERNMENT RIGHTS

This invention was made with government support under Grant Nos. R21 EB020096 and P41 EB017183, both awarded by the National Institutes of Health. The government has certain rights in the invention.

FIELD OF THE INVENTION

The present invention generally relates to magnetic resonance imaging.

BACKGROUND OF THE INVENTION

Magnetic Resonance Fingerprinting (MRF), a technique recently introduced by Ma, et al., 2013, represents a paradigm shift for Magnetic Resonance Imaging (MRI). In contrast to conventional imaging strategies, where the desired image is directly encoded in the frequency domain (Bernstein, et al., 2004), in MRF a parameter map is constructed from a time-series of highly under-sampled images. Although none of the individual snap-shots in a MRF experiment yields an accurate anatomical image, the complete set captures the time dependent spin evolution. When a suitably optimized MRF sequence is used, the measured signal timecourse represents a unique "signature" identifying the underlying tissue properties in each voxel. Simulating, for a plethora of tissue and environmental parameters, the spin-dynamics induced by the sequence, a dictionary is constructed that relates each signature to the corresponding tissue properties. Finally, the desired parameter map(s) are reconstructed by identifying, for each voxel independently, the dictionary element best matching the measured signature. This map provides quantitative information about the bulk spin properties such as T1 and T2 (among others), allowing various tissues to be differentiated.

Over the years many techniques have been proposed to accelerate the acquisition process by under-sampling the frequency domain (k-space) representation of an image (Sodickson, et al., 1997; Preussmann, et al., 1999; Griswold, et al. 2002; among others). In short, these methods exploit the different receive sensitivities profiles provided by an array of receive coils to reconstruct the missing k-space data. In general, each coil has a distinct transmit- and receive-sensitivity profile (Hoult, 2000a). Traditionally, non-uniformities in the transmit-sensitivity are considered undesirable, giving rise to contrast artifacts and areas of shading in the final image. To achieve a satisfactorily uniform excitation, clinical systems typically use a large quadrature birdcage-coil for transmission. To enable parallel imaging, said systems are complemented by a set of dedicated receive array coils.

During a conventional MRF experiment, a series of images is obtained in rapid succession. To this end, following each RF pulse, a spiral readout trajectory is used to obtain a series of under-sampled images. Moreover, each of these readouts is highly under-sampled to minimize the minimum time between snapshots. Although parallel-imaging techniques could in principle be used, the images are reconstructed without the aid of said techniques. This results in strong aliasing artifacts. To minimize artifacts in the final parameter map, the orientation of the readout trajectory is changed between snapshots. Although each image will still contain strong artifacts, the aliasing patterns will be different. Following the signal measured in a single voxel through the stack of images, the incoherent artifacts add a noise like component to the measured signal evolution. It has been shown that when a large number of snapshots is acquired, e.g. 1000 images with 128×128 matrix size, the time-dependent signals can still be used to identify the underlying relaxation parameters of the tissues (Ma, et al., 2013).

In pursuit of ever more detailed anatomical images, increasingly high field strength systems have been constructed to reap the benefits of the increased signal strength. However, the Larmor frequency increases linearly with field strength, resulting in increasingly significant interactions between applied radiofrequency (RF) fields and tissue. For certain systems the RF wavelength is comparable to the dimensions of the human torso, resulting in contrast artifacts and areas with signal voids in the abdomen (Bernstein, et al., 2006). Considering research systems currently operating at 7 to 11.7 Tesla, strong RF interference effects result in extremely non-uniform transmit-sensitivity ($B_1^+(r)$) profiles (Yang, et al., 2002).

Many techniques have been proposed to mitigate spatial variations in the transmit-sensitivity profile (Hoult. 2000b; Katscher et al., 2003; Bernstein, et al., 2004; Zhu, 2004; Seheako et al., 2006; Boulant, et al., 2008; among many others). Among the most promising techniques published to date is parallel transmission (Katscher et al., 2003; Zhu, 2004). Inspired by parallel imaging, parallel transmission was introduced as a framework to capitalize on the unique sensitivity profiles provided by an array of transmits coils. Rather than accelerating the acquisition process, parallel transmission is used to reduce the duration of subject specific rf-pulses, and also to facilitate the shaping of tailored excitation profiles via interference between fields generated by distinct coil elements. These tailored excitations have been shown to provide excellent mitigation of $B_1^+(r)$ non-uniformity (Setsomopop et al., 2008; Cloos et al., 2012a, 2012b). Alternatively, this technique can also be used to reduce the field of view (Schneider et al., 2013), allowing the operator to "zoom in" on a given area of interest.

In 2010, Katscher, et al. published a paper describing an attempt to use the distinct sensitivity profiles in a transmit-array to reduce the number of phase encoding steps necessary to reconstruct a conventional MR image. However, they highlight that this is extremely tedious due to the tendency of non-uniform transmit-sensitivity profiles to form contrast artifacts. To minimize these adverse effects, Katscher, et al. 2010 focuses on the diversity in the transmit-phase while striving to maintain reasonable amplitude uniformity. Moreover, the repetition time was lengthened to minimize relaxation effects. Consequently, both the acquisition speed and the obtainable contrast, both high priorities for clinical imaging, are greatly impaired.

SUMMARY OF THE INVENTION

One embodiment of the invention relates to a system for whole body magnetic resonance imaging. The system includes a magnet and a plurality of radio frequency transmitters in communication with a computer system each independently driving a coil element, coil mode, or subgroup of linked coil-elements. Each of the plurality of independently driven coil elements (or groups of coil elements) produces a distinct B1+.

One embodiment of the invention relates to a nontransitory computer-readable memory having instructions thereon. The instructions are for transmitting a radio frequency signal from a plurality of coil elements, where each of the plurality of coil elements transmits an independent radio frequency signal producing a distinct B1+. Additional instructions provide for receiving induced radio frequency signals from a material. Additional instructions provide for identifying the material based upon the closest match utilizing the distinct B1+ associated with each of the plurality of coil elements.

One embodiment of the invention relates to a method for identifying a material. A radio frequency signal is transmitted from a plurality of coil elements, where each of the plurality of coil elements transmits an independent radio frequency signal producing a distinct B1+. Induced radio frequency signals are received from a material. The material is identified based upon the closest match utilizing the distinct B1+ associated with each of the plurality of coil elements.

One embodiment of the invention relates to a system for magnetic resonance fingerprinting in the presence of strong $B_1^+(r)$ non-uniformities comprising a processor and tangible computer-readable medium operatively connected to the processor. The computer readable medium includes computer code configure to receive magnetic resonance information regarding a material including B1+ information, search a database having an MRI library for a closest match to the received magnetic resonance information, and identify the material based upon the closest match.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIGS. 7A-D are a quantitative comparison of IRTSE- and MR-PTX-fingerprinting-based T1 maps at 7 T, FIG. 7A illustrates an IR TSE Series, FIG. 7B illustrates an MR Fingerprint at Location A and B, FIG. 7C illustrates a zoomed section of a TSE T1-map with location A and location B indicated, and FIG. 7D illustrates a zoomed section of a TSE T1-map with location A and location B indicated.

FIG. 8A illustrates reconstructed set of $B_1^+$ maps, FIG. 8B illustrates a T1 map, FIG. 8C illustrates a T2-star image and FIG. 8D illustrates relative $B_1^-$ maps derived from a single 15 s acquisition.

DETAILED DESCRIPTION OF THE PREFERRED EMBODIMENTS

Figure 1:
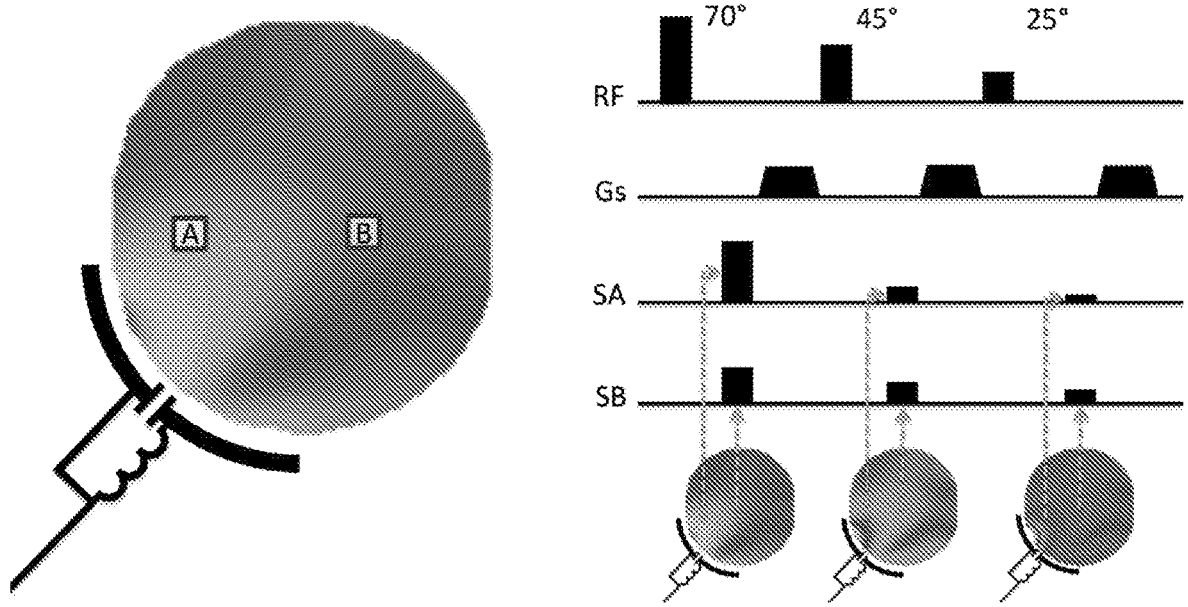
FIG. 1 illustrates on the left hand side, the transmit-sensitivity profile is shown corresponding to a single surface coil (axial plane). On the right hand side, a simplified schematic overview of a spoiled gradient recalled echo based MRF sequence is shown, where RF indicates the nominal flip-angle specified in the sequence, Gs the location of the spoiler gradient, and SA and SB the measured signal corresponding to locations A and B in the axial plane.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

In one implementation, a general framework is for signal encoding in MRF that enables simultaneous transmit and receive encoding to accelerate the acquisition process, or improve the fidelity of the final image/parameter-map per unit scan time. The proposed method and systems capitalize on the distinct spatial variations in the sensitivity profile of each transmit-coil to reduce the acquisition time, and/or improve the fidelity of the final parameter-map per unit time. The techniques described here provide several major applications, though are not limited to the listed:

1) The proposed method provides a robust and fast way to perform MRI in the presence of strong $B_1^+(r)$ (the component that rotates in a plane perpendicular to the static magnetic field in an MRI machine) variations. In contrast to techniques currently available, such as parallel-transmission (Katscher et al., 2003; Zhu, 2004), it does not require extensive patient specific calibrations. Moreover the solution is generic and does not require optimization for each individual application/patient. In contrast to other $B_1^+(r)$ insensitive solutions, such as adiabatic pulses, the proposed technique uses standardized short and low SAR RF-pulses that have been successfully used for many years in all clinical MRI systems (square, sinc, SLR, etc).

2) A practical workflow for whole body MRI at ultra-high field (7 Tesla and up).

3) The reduction of coherence between aliasing artifacts. This can be used to reduce the number of snapshots (acquisition time) while maintaining the fidelity of the final parameter map. Alternately this can be leveraged to increase the quality of the final map.

4) The unfolding of aliased voxels based on the available transmit-sensitivity profiles enabling higher-resolution parameter maps to be obtained in an equivalent unit of scan time. If the same resolution is used, the method can be used to reduce the scan time or increase the fidelity of the final parameter map.

In one implementation, systems and methods provide for imaging in the presence of strong $B_1^+$ non-uniformities. In the published MRF experiments a spatially uniform $B_1^+$ was assumed. Consequently, the dictionary of simulated spin-evolutions ("signatures") only contains signatures corresponding to the flip-angles prescribed in the sequence. "Flip-angles" refer to the angle of excitation for a field echo pulse sequence, i.e. the angle to which the net magnetization is rotated or tipped relative to the main magnetic field direction via the application of an RF excitation pulse at the Larmor frequency. When using a suitable transmit-coil at relatively low field strength, e.g., 1.5 Tesla, this dictionary is sufficient to recover the final parameter map. However, at higher field strengths it becomes increasingly difficult to maintain a high level of homogeneity. In one implementation, rather than focusing on methods to mitigate these effects, the focus is to exploit the non-uniformities in $B_1^+(r)$.

On the left hand side of FIG. 1 the $B_1^+(r)$ corresponding to a single surface coil at 7 Tesla is shown (simulated using microwave studio 2012, Framingham, Mass., USA). For a given driving voltage, the two highlighted locations (A and B) experience a different transmit-field amplitude and phase. Considering the non-linear Bloch equations (Bloch et al., 1948), the spin-evolution measured with an MRF sequence will be different at these locations even if the tissue properties are the same (FIG. 1 SA & SB). Consequently, information about the spatial location of the signal origin is encoded into the spin-evolution, i.e., the measured time dependent signals SA(t) and SB(t).

The above-described behavior can be understood by considering, for example, a spoiled gradient recalled echo sequence (Bernstein et al., 2004). When using a single surface coil, the nominal flip-angle is only calibrated on a small region of interest. Suppose the calibration was performed on area A, such that the flip-angle induced by the first RF-pulse in this area will be 70°. Starting from a normalized initial net-magnetization $\rho_0=1$, a large transverse component is created and a strong MR signal is produced at this location (Eq. 1).

$$SA(1) = \rho_0 \sin\left(\frac{\pi}{180} 70\right) \approx 0.94 \qquad \text{Eq. 1}$$

After the signal is acquired, a gradient is applied that de-phases the transverse magnetization. Using a TR<<T1, the net magnetization available for the second pulse to act on is $\rho_{1A} = \rho_0 \cos(70 \pi/180)$. The second pulse, in this case 45°, now only induces a relatively small transverse component resulting in a reduced signal (Eq. 2).

$$SA(2) = \rho_{1A} \sin\left(\frac{\pi}{180} 45\right) \approx 0.24 \qquad \text{Eq. 2}$$

Consider location B with the same normalized initial net magnetization. Due to the non-uniformity in the transmit-sensitivity profile, the first pulse will induce a much lower flip-angle (~30°) resulting in a smaller signal (Eq. 3).

$$SB(1) = \rho_0 \sin\left(\frac{\pi}{180} 30\right) \approx 0.5 \qquad \text{Eq. 3}$$

The next pulse will also induce a smaller flip-angle than at location A (~20° vs 45°). However, at location B the transverse magnetization following the first excitation was much smaller. Consequently, the net magnetization available after spoiling is much larger ($\rho_{1B} = \rho_0 \cos(30\pi/180)$) and the signal obtained at B now exceeds what is measured at location A. (Eq. 4).

$$SB(2) = p_{1B}\sin\left(\frac{\pi}{180}20\right) \approx 0.30 \qquad \text{Eq. 4}$$

To retrieve the parameter map from an MRF experiment performed using a non-uniform $B_1^+(r)$, the dictionary must be extended to encompass variations of the sequence where the induced flip-angles are scaled by a complex weighting factor. Searching the entire dictionary for the best match provides, in addition to the usual parameter map(s), a $B_1^+(r)$ map. Alternatively, if $B_1^+(r)$ is known from an earlier measurement (Stollberger, et al., 1996; Yarneky 2007; Nehrke et al., 2012; among others), the search space can be constrained by considering only those entries that match the measured $B_1^+(r)$.

The above equations (1-4) correspond to analytic solutions assuming perfect spoiling in a gradient echo sequence and neglecting relaxation effects. In practice the full Bloch equations are to be considered so as to obtain a highly accurate representation of the spin-dynamics including spoiling imperfections and relaxation effects. Moreover, different sequence configurations, such as spin-echo, balanced SSFP, or others, all show a $B_1^+(r)$ dependent signal evolution.

In another implementation, system and methods provide a practical workflow for whole body MRI. In one implementation, the whole body MRI is at ultra-high field (7 Tesla and up). When utilizing a single transmit-coil, areas further from the element may be hampered by the relatively low transmit-sensitivity. Although the spatial variations in $B_1^+(r)$ are now accounted for, it remains difficult to induce a substantial flip-angle in areas where the transmit-sensitivity is very low. Ultimately this will result in a poor signal to noise ratio and reduced orthogonality between "signatures".

Figure 2:
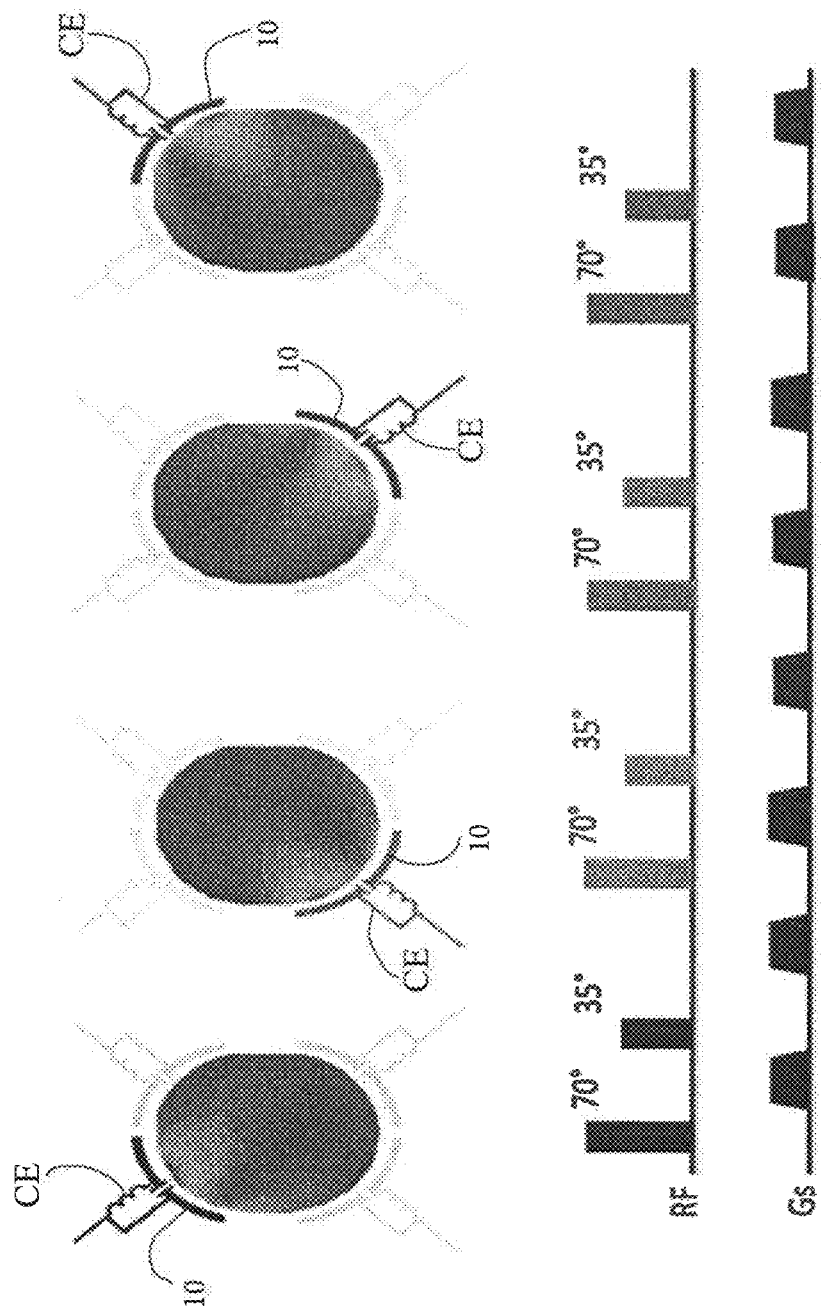
FIG. 2 is an illustration of the use of multiple transmit-elements (including RF transmitters 10) to accelerate an MRF sequence or mitigate signal dropout in a large field of view. The top row shows the transmit-sensitivity profiles corresponding to four coil elements CE distributed around the object. On the bottom a simplified sequence diagram is shown illustrating how the different coil-elements CE can be incorporated in to the sequence.

Distributing multiple independently driven coil-elements around the object improves coverage and provides a range of unique transmit-sensitivities for encoding (FIG. 2, top). Utilizing parallel-transmit hardware, the proposed encoding mechanism can capitalize on the distinct $B_1^+(r)$ associated with each coil (FIG. 2, bottom). Using different coil combinations for transmission the spins are influenced by many different $B_1^+(r)$. This solves the problems caused by signal voids due to destructive interferences encountered when performing B1-shimming or using volume coils at ultra-high field (7 Tesla or higher). As long as every point in the volume of interest is illuminated by at least one of the coils, a substantial transverse magnetization will be induced and a viable signature can be measured. In contrast to a traditional RF-shimming experiment, the proposed approach is not limited to one fixed combination of coils. Electro dynamics imposes strong limitations on the transmit uniformity achievable using RF-shimming. In the proposed different coils or coil combinations can be used sequentially. This ensures adequate excitation through a large field of view.

To reconstruct a MRF data set encoded with multiple transmit-coils the dictionary must include all possible combinations of sensitivities. Although this requires a much larger dictionary, accurate $B_1^+(r)$ measurements can be used to constrain the search space to that of a conventional MRF experiment. In other words, considering only those dictionary elements that correspond to the sensitivities measured in a given voxel, the reconstruction time can be reduced to that of a conventional MRF experiment. From a practical perspective, the need for time consuming high quality calibration scans is undesirable. Considering that, even at ultra-high field, the sensitivity profiles only contain smooth spatial variations, extremely fast and low-resolution $B_1^+(r)$ measurements can be employed to constrain the search space to a manageable size. Moreover, provided that the transmit-sensitivities are sufficiently distinct, searching the complete dictionary allows the $B_1^+(r)$ maps to be derived without the need for a calibration scan, see, e.g., FIG. 8A. Consequently, in contrast to conventional parallel-transmission methods, the time consuming calibration scans can be reduced to a minimum or even omitted entirely. Moreover, the proposed method is generic and does not require any patient specific optimization. Thus providing a plug and play solution for MRI at ultra-high field strengths.

In another implementation, the system and methods may be utilized for the reduction of coherence between aliasing artifacts. In addition to providing an enhanced illumination of the sample, varying the effective $B_1^+(r)$ reduces the coherence of under sampling artifacts in the MRF signature. Because multiple spatially different transmit-sensitivities are used, each of the snapshots will be more distinct from one another. Drawing an analogy to photography, this effect is similar to what would happen if you take multiple pictures of a single object while using a flashlight to illuminate it from different angles. In the context of an MRF experiment, this will improve the ability to match the measured signal evolution to the corresponding element in the dictionary. This reduced coherence can also be exploited to decrease the number of snap-shots, i.e., acquisition time, while maintaining the same level of accuracy in the final parameter map.

Figure 3:
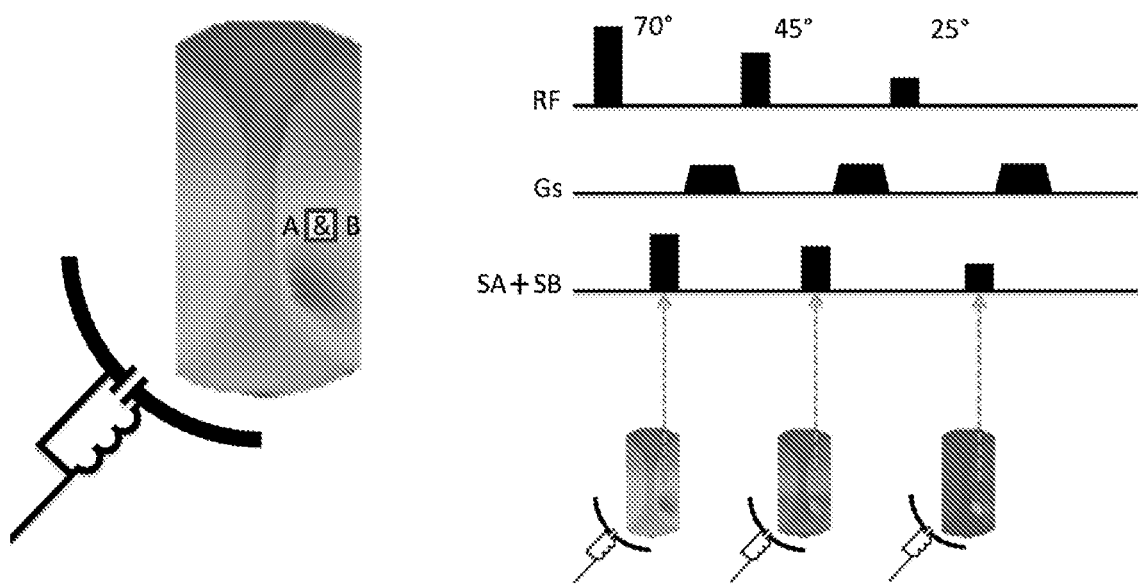
FIG. 3 illustrates on the left hand side, the two locations marked in FIG. 1 are shown again. This time due to the acceleration factor of 2, the voxels are aliased and now lie on top of one another in the image. On the right hand side, a schematic overview of a spoiled gradient recalled echo based MRF sequence is shown, where RF indicates the nominal flip-angle used, Gs the location of the spoiler, gradient and SA+SB the measured signal corresponding aliased voxels A and B.

In another implementation, systems and methods may be utilized for the unfolding of aliased voxels based on the available transmit-sensitivity profiles. The benefits of using non-uniform transmit-sensitivities can also be revealed by considering the reconstruction of an under-sampled data set. Consider an MRF data set acquired while skipping every other line in k-space, i.e. using an -under-sampling factor of 2. Without the aid of parallel imaging techniques a series of aliased images will be obtained. Consequently, each voxel represents the superposition of two signals originating from different locations in the object. In terms of an MRF experiment this means that the measured signal is the complex addition of two distinct signatures (FIG. 3).

Figure 4:
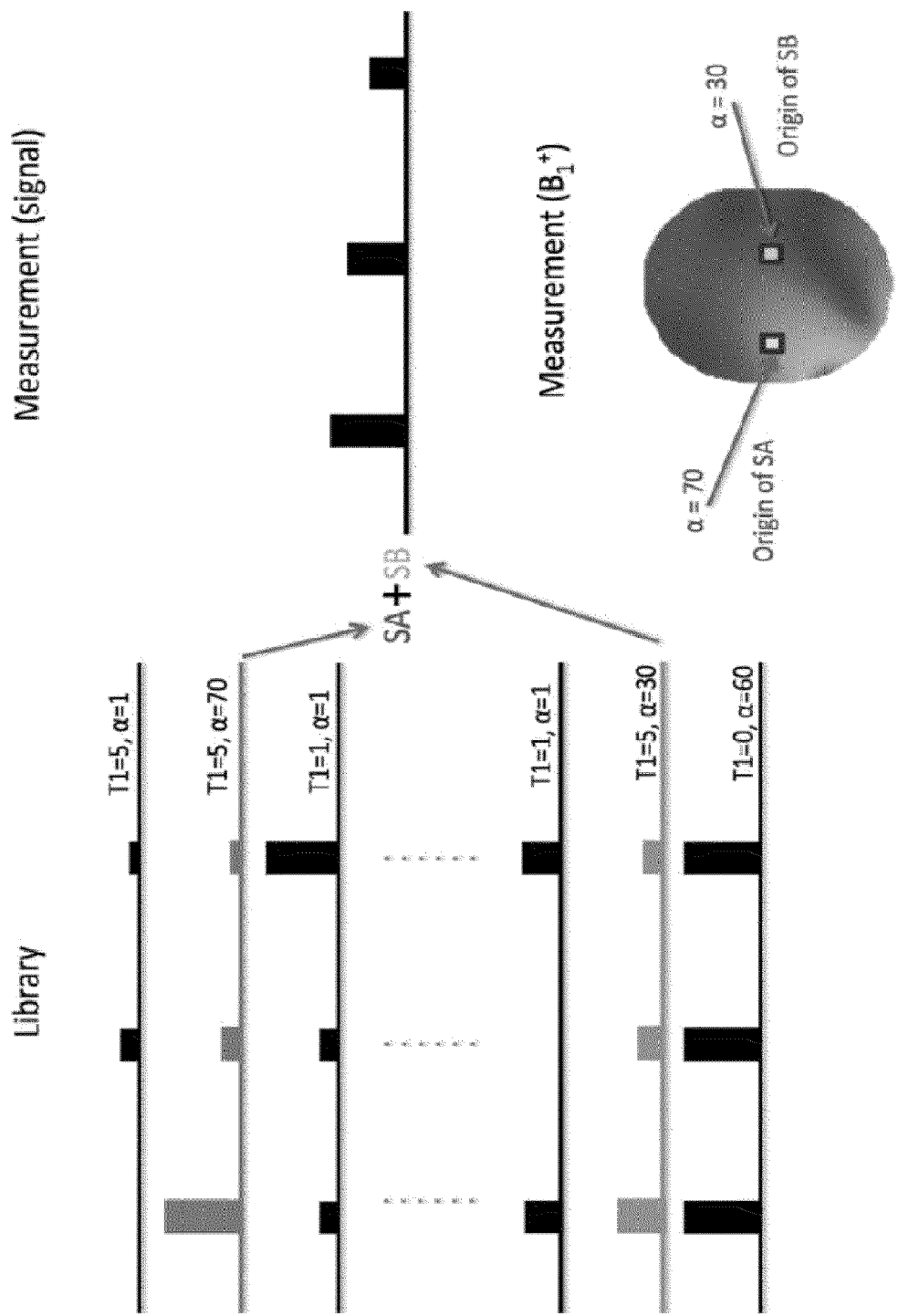
FIG. 4 illustrates the reconstruction process for the unfolding of an aliased image based on the transmit sensitivity profiles. The measured signal (SA+SB) is compared to all possible combinations of dictionary elements. The best match relates the underlying tissue properties to the aliased voxel. The location of each signature SA and SB can be resolved by localizing the nominal flip-angles associated with the signature to the B1+ map. The B1+ map can also be used to constrain the search to dictionary elements with the correct nominal flip-angle (and search for the corresponding T1 & T2 values, among other desired parameters).

When $B_1^+(r)$ is known the aliased signatures can be unfolded (FIG. 4). Instead of searching for the single best match in the dictionary, for every voxel 2 dictionary elements are sought that, when added together, best match the measured signal (complex addition). Once found, the locations from which signatures originated can be identified by matching the effective flip-angles associated with the simulated MRF signatures to the $B_1^+(r)$ map. In general, to unfold an N times accelerated data set the optimal superposition of N dictionary elements must be identified. Un-ambiguous signal localization requires that none of the aliased voxels experience the exact same $B_1^+$. However, voxels that did not fold on to one another may experience the same $B_1^+$ without impeding the reconstruction process. Consequently, a stronger $B_1^+(r)$ in-homogeneity will generally improve the reconstruction.

Whereas parallel-imaging techniques allows the unfolding of aliased voxels in image space, the proposed transmit-sensitivity based method provides a means to unfold aliased MRF signatures. Consequently, the proposed technique can be combined with parallel imaging to further accelerate the acquisition process or improve the final image quality. Much like parallel imaging, increasing the number of independent transmit-elements increases the maximum obtainable acceleration factor. Apart from MRF, considering the "signature" produced by a spin-echo train, the proposed method is also applicable to the model driven parametric mapping techniques proposed by Ben-Eliezer, et al 2013.

Although the experimental setup is similar to those used in conventional MRI including parallel transmission, the proposed technique is fundamentally different from what was proposed in Katscher et al., 2003, Zhu, 2004 or Katscher et al 2010. In particular, the proposed invention encodes spatial information into the MRF "signature", i.e., using the transmit-sensitivity profile(s) to encode spatial information regarding the signal origin into the spin evolution. In contrast to Katscher et al 2010, the method proposed here thrives on increasingly non-uniform transmit-sensitivities (amplitude and phase), is free from assumptions regarding relaxation, allows short repetition times, and is less prone to result in high local specific absorption rates.

Unlike prior systems relying on a single coil, in one implementation, multiple B1+ distributions are solved for at once. In MRI traditionally one B1+ field is considered, which is generated by a single coil or possibly an ensemble of coils with fixed phase and amplitude relations (RF-shimming). It is important to note that at high field strengths any given ensemble of coils driven with a fixed amplitude and phase combination will only produce a uniform B1+ field in a small region of interest. When targeting, for example, an axial slice in the torso at 7 T it is impossible to uniformly excite the entire region using RF-shimming. Due to destructive interference between fields areas with almost no excitation will form.

Although parallel transmission can produce a uniform excitation in such regions, it still only considers the flip-angle distribution induced by PTX system at the end of each RF pulse, i.e. a "virtual transmit sensitivity". One could utilize a derivative approach to combine such pulses with the MRF technique, but it still requires the cumbersome workflow associated with parallel transmission (time consuming calibration scans and pulse design).

Essentially, in one implementation the individual images are no longer the focus. Instead the focus is obtaining uniquely identifiable "signatures". The field of view at high field can be dramatically improved by interleaving multiple transmit sensitivities because this circumvents destructive interference of the field components produced by each of the coils. Consequently, as long as a coil in the ensemble has adequate B1 in the field of view, a viable parameter map can be constructed. In traditional MRI this would cause enormous contrast artifacts and render the final image unusable for diagnostic purposes.

However, utilizing the systems and methods described herein these same artifacts now provide vital information about the underlying spin dynamics i.e. produce more unique signatures. This enables high fidelity parameter maps covering a large field of view even at ultra-high field strengths to be obtained. Multiple different transmit-sensitivities are introduced in to the sequence to create more unique signatures and reconstruct the parameter maps and multiple B1-maps from a single dataset guarantees high fidelity tissue property maps and circumvents the need of time consuming calibrations scans traditionally associated with parallel transmission.

EXPERIMENTAL EXAMPLES

Parallel transmission (PTX) is often proposed as a framework for transmit non-uniformity mitigation in ultra-high field MRI (7 Tesla). However, routine application of PTX has hitherto been hampered by technical challenges. In particular, optimal performance is contingent on high quality subject-specific transmit-sensitivity ($B_1^+$) maps. Despite major advances in $B_1^+$ mapping the necessary calibration scans still impose a significant time penalty on each PTX exam. Moreover, tailored pulse design, needed to achieve high fidelity excitations covering an extended region of interest, remains a computationally demanding and technically challenging endeavor impeding workflow by adding additional delay times between scans.

When image data are acquired in quick succession, the time course of the signal can be matched to a pre-calculated library of simulated spin evolutions. As demonstrated by Ma, et al, when using a suitable encoding scheme, finding the optimal match can reveal quantitative information about the underlying tissue properties. Extending the parameter space covered by the library enables the simultaneous quantification of the $B_1^+$ field. However, the signal level obtained from areas with extremely low $B_1^+$ remains compromised. To secure adequate signal throughout the field of view, the individual transmit channels have been interwoven during the encoding of the MR fingerprint. Not only does this circumvent RF-interference effects between coils, which could result in signal voids or Specific Absorption Rate (SAR) hotspots, it also serves to reduce the coherence between reconstruction artifacts and enables the identification of the underlying $B_1^+$ components corresponding to each of the transmit-channels. Spoiler gradients were inserted to decouple the transmit-phases between channels allowing the reconstruction to focus on the longitudinal relaxation (T1), each of the $B_1^+$ and relative receive sensitivities ($B_1^-$), as well as a Proton Density or T2-star weighted image.

Figures 5A, 5B:
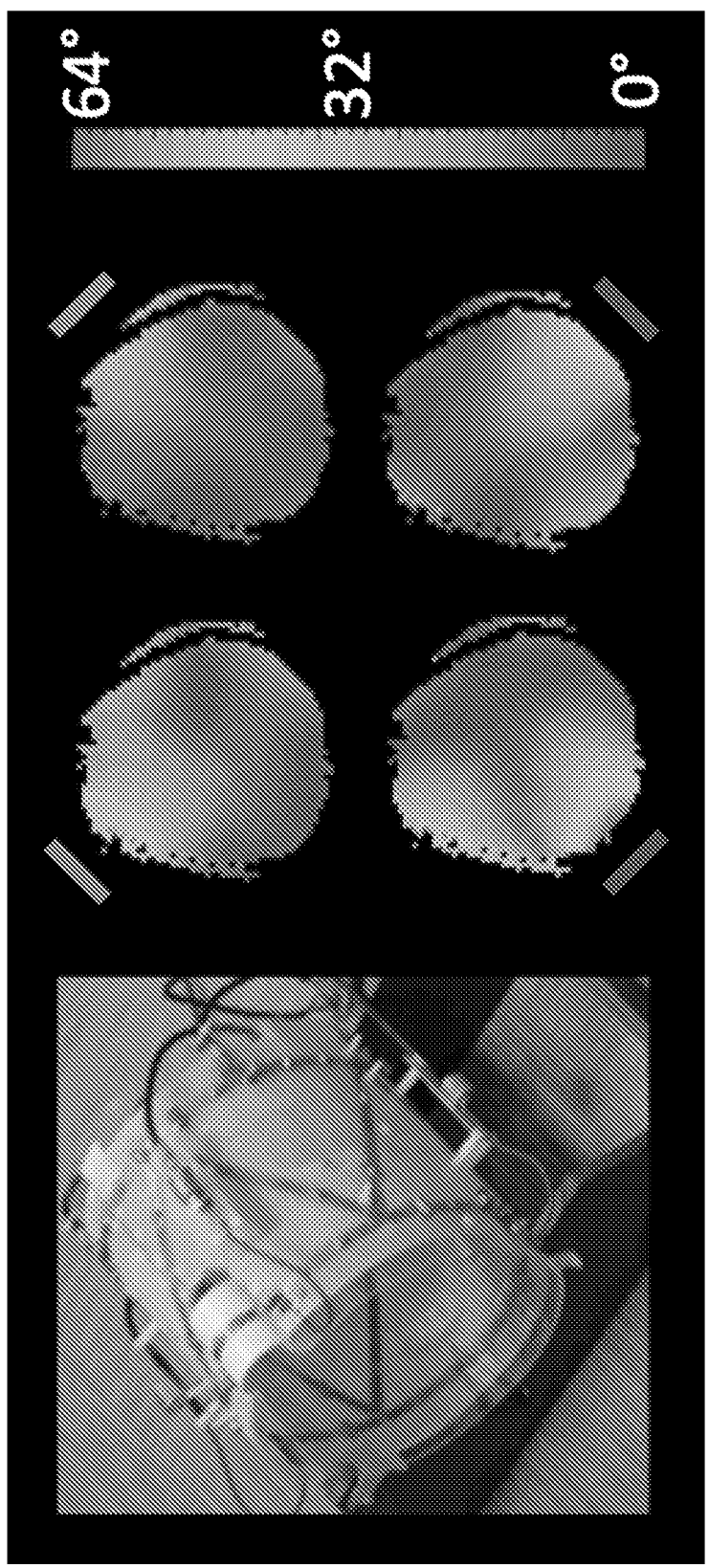
FIG. 5A illustrates one implementation of a triangular transceiver-array and FIG. 5B illustrates transmit sensitivity profiles corresponding to the elements used in the experiments. $B_1^+$ maps were acquired using the AFI sequence.
Figure 6:
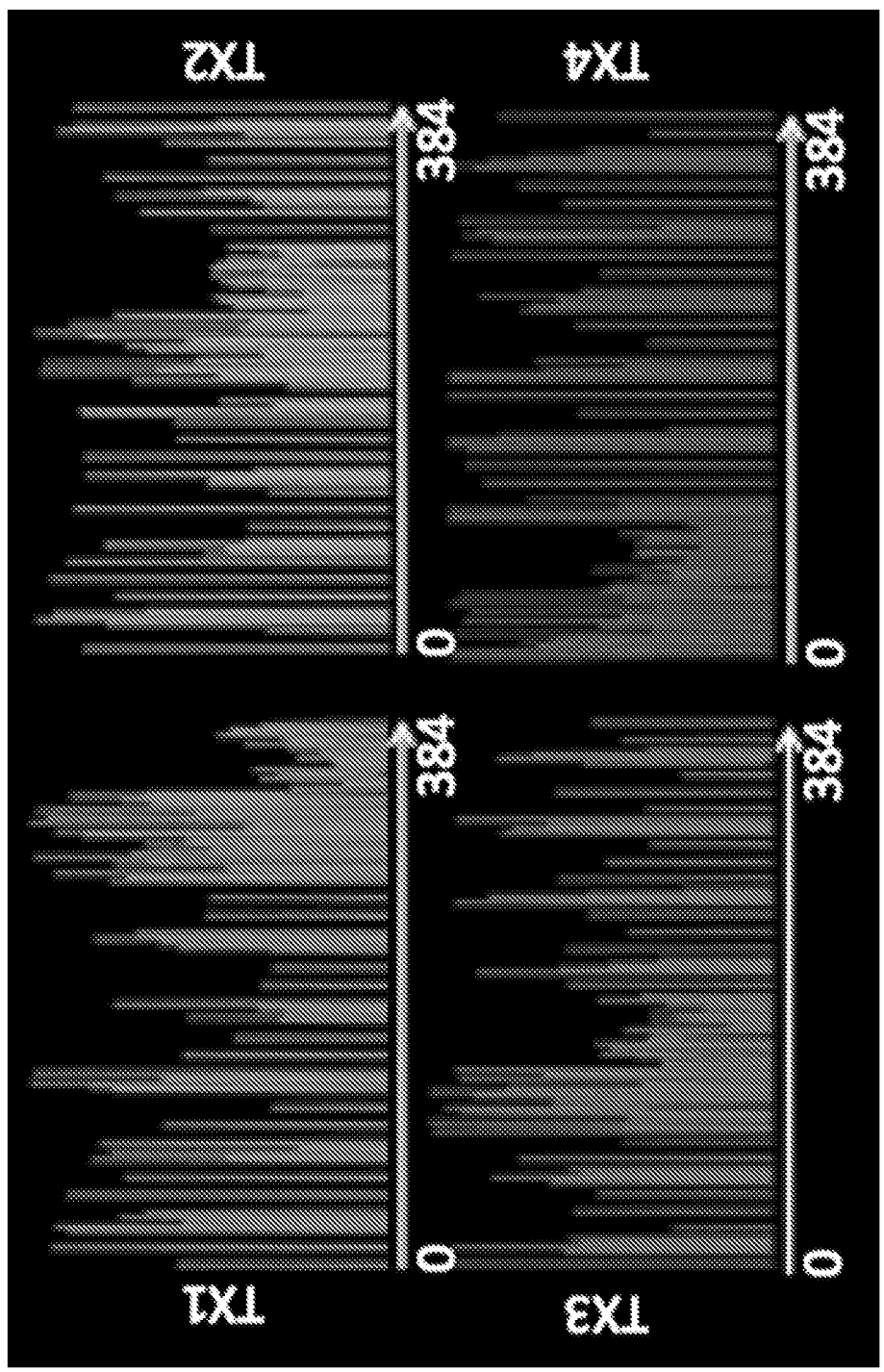
FIG. 6 illustrates different RF-pulse amplitudes played on each of the channels throughout the acquisition of a single slice. Channel color-coding is in accordance with FIG. 5.

Methods:

Experimental validation was performed on Magnetom 7 T and 9.4 T MRI systems each equipped with 8 channel PTX capability (Siemens, Erlangen, Germany). In this initial demonstration only 4 transmit channels were used (FIGS. 5A-B). To this end, the upper 4 channels of a triangular array at 7 T and a dual-row transmit array at 9.4 T were used. A balanced energy distribution among coils is desired to ensure an even illumination of the field of view and prevent formation of SAR hot spots. This was achieved by concatenating (twice) the ordered set of 4-tuples, resulting in 384 snapshots of the spin evolution (FIG. 6). To further increase the dynamic range, the transmit voltages on individual channels were pseudo-randomly modulated between 0.25 and 1. Imaging parameters (at 7 T/9.4 T) were 3×3/2×2 mm in-plane resolution, 5/2 mm slice, TR=40/40 ms, TE=19/15 ms, Echo Planar Imaging (EPI) readout, total scan time 15 s. The library of simulations was constructed using in-house developed software based on the formalism described by Benoit-Cattin, et al. The gradient ascent algorithm was used to quickly find the best matching fingerprint based on the correlation. Once the optimal match was found, the relative $B_1^-$ profiles were retrieved by calculating the scaling factor with the simulated fingerprint as observed by each receiver. Similarly, the same procedure was applied to the combined data to retrieve a T2 star weighted image. The reconstructed $B_1^+$ maps were validated against the well-established Actual Flip-Angle Imaging method (AFI, TR1/TR2=40/200, TE=4.5 ms, total scan time ~10 min). For validation, the circularly polarized mode (using all 8 channels) was used to create a T1 map based on a series of Inversion Recovery Turbo Spin Echo (IRTSE) images (T1={0.05, 0.1, 1, 2, 9 s}, TR=10 s, TE=12 ms, Turbo Factor 5, iPAT 2, 1.65×1.65 mm, 5 mm slice, total scan time ~15 min). A 16 cm diameter two-compartment phantom (0.5 g NaCl per 750 cl $H_2O$, doped with 0.5 ml or 1.0 ml gadolinium) phantom was used for in-vitro validation. In-vivo data were acquired in the human brain at 7 T and 9.4 T in accordance with the IRB of the relevant institutions.

Figures 9A, 9B:
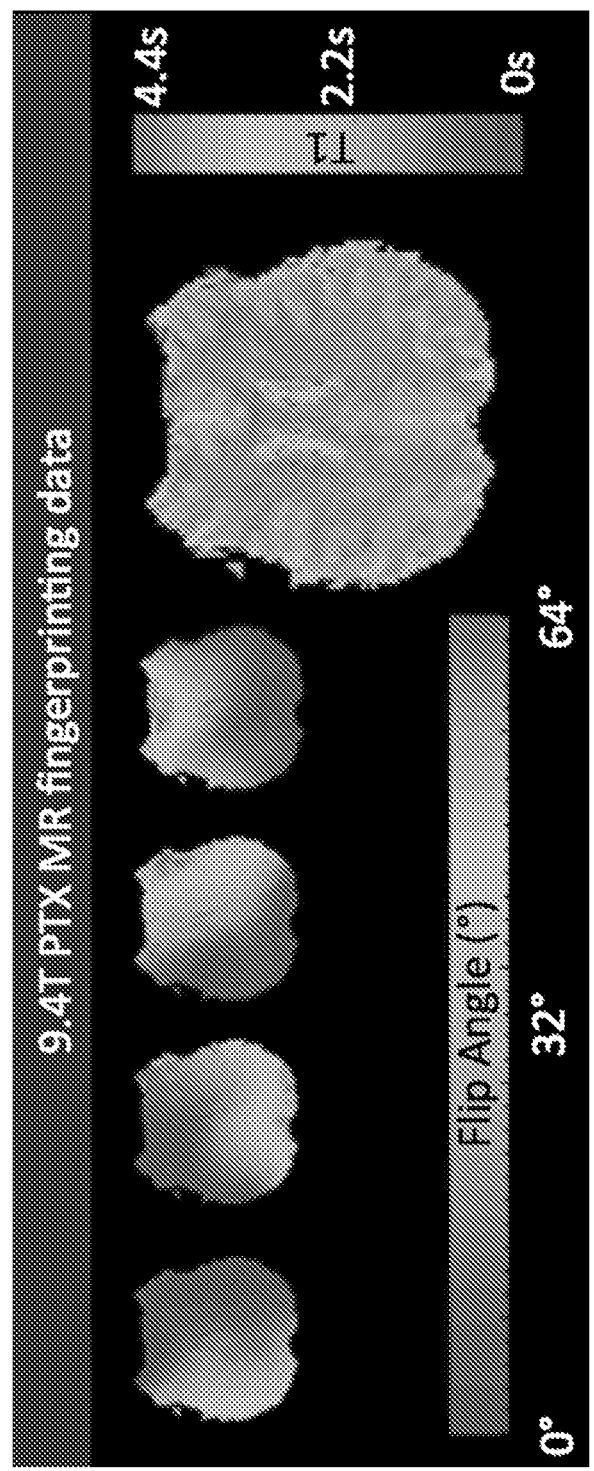
FIG. 9A illustrates reconstructed $B_1^+$ maps and FIG. 9B illustrates a T1 map using the PTX MRF method at 9.4 T where traditional imaging method suffer greatly from transmit sensitivity non-uniformities.

Results:

The $B_1^+$ maps measured in the phantom all demonstrated a correlation above 0.93 (0.95±0.01) with their AFI counterparts. Phantom T1 values (compartment 1/compartment 2) were; 775±38/312±27 vs 756±15/346±10 for the proposed and the traditional IRTSE-based method, respectively. The top part of FIG. 7A-D shows the series of IRTSE images and a zoomed section of the reconstructed T1-map at 7 T. The bottom part shows two fingerprints associated with the approximate locations A and B in the zoomed images (FIG. 7A-D). Throughout the brain the optimal matches resulted in correlation factors above 0.99. The T1 values measured with the proposed approach were in excellent agreement with existing literature values (A=1.2 s, B=4.4 s)[11]. On the other hand, the IRTSE based maps appear to underestimate the T1 in the spinal fluid. The in-vivo measured $B_1^+$ maps also showed excellent agreement (correlation factor of 0.96±0.01) with the AFI measurements (FIG. 8A-D). At 9.4 T, where the IRTSE was compromised by the transmit voltage and SAR limitations (on top of the expected increase in $B_1^+$ non-uniformity), the proposed approach retained high-quality quantitative information (FIGS. 9A-B).

Discussion:

The simultaneous quantification of both T1 and multiple $B_1^+$ maps within a scan time of only 15 s was demonstrated. Apart from the inherent robustness to subject motion in an MRF-type experiment, the reduced scan time by over one order in magnitude compared to the IRTSE offer practical advantages when scanning a less compliant subject. Admittedly, at the expense of increased SAR, the IRTSE could be run in an interleaved multi-slice fashion. Nonetheless, even when acquiring 40 slices the proposed approach would still be 50% faster. Moreover, the proposed approach does not rely on high-fidelity inversion or refocusing pulses, nor does the SAR increase with the number of slices. Consequently, the energy deposition is reduced substantially due to the lower flip-angles involved, and omission of energy demanding $B_1^+$ insensitive RF-pulse solutions. Application of this calibration free PTX framework to other parts of the body requires better resilience against chemical shift and off-resonance effects than is possible with the EPI acquisition used in this work. To this end we are currently exploring spiral-based readout trajectories with an incremental golden angle in plane rotation to minimize the coherence of these artifacts in the fingerprint. To enable the simultaneous quantification of T2, we plan to explore a selective spoiling scheme to decouple the relative transmit-phases.

Conclusion:

A novel approach to excitation non-uniformity mitigation at UHF was demonstrated that utilizes the PTX setup without the need for cumbersome calibration scans or tailored pulse design. It enables fast simultaneous quantitative mapping of the T1 relaxation time and an array of transmit sensitivity profiles in less than 15 s.

Additional Experimental Examples

Further, under some circumstances, complex electrodynamic interactions between a subject and an incident RF field may distort RF excitation to such an extent that the diagnostic value of MRI be compromised (Bernstein, 2006). Metal implants, in particular, are a source of MR artifacts, resulting not only from distortion of the main magnetic field, but also from distortions of the excitation RF field (Graf et al., 2005). In at least one example, the potential of a generalized implementation of a proposed plug & play parallel transmission (PTX) framework (Cloos et al., 2014) was considered to enable rapid multiparametric mapping (T1, T2, PD) in the presence of orthopedic implants.

Figure 11A:
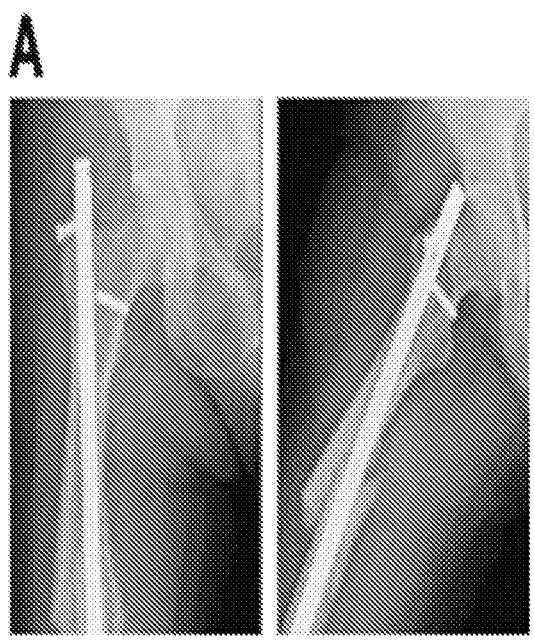
FIG. 11A illustrates an X-ray image showing a location of an orthopedic implant (a titanium rod approved for 3 T MRI).
Figure 11B:
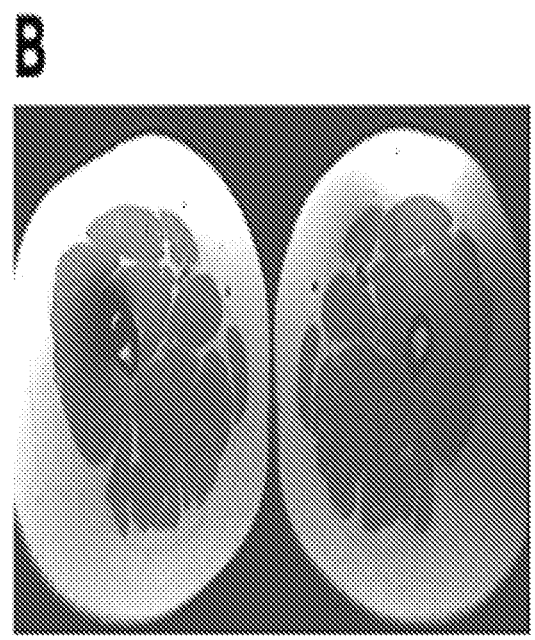
FIG. 11B illustrates an axial turbo spin echo image with a $B_1^+$ artifact near the implant due to interactions with the incident RF field (3 T).

At 3 Tesla, large metal implants such as the titanium rod depicted in FIG. 11A may interact significantly with the incident RF field. Depending on the polarization of the applied RF field, different reactive fields are produced, which in turn perturb the uniformity of the excitation. When a single RF transmitter (e.g., an RF transmitter 10 as shown in FIG. 2) configuration is used, such as the circularly polarized mode of the birdcage coil, a signal void may appear in the image, as shown in FIG. 11B. However, each of the two linear modes, traditionally combined together to comprise the quadrature excitation, interact differently with the implant. By driving these modes independently, complementary field distributions may be formed to secure sufficient signal throughout the field of view.

Figure 12:
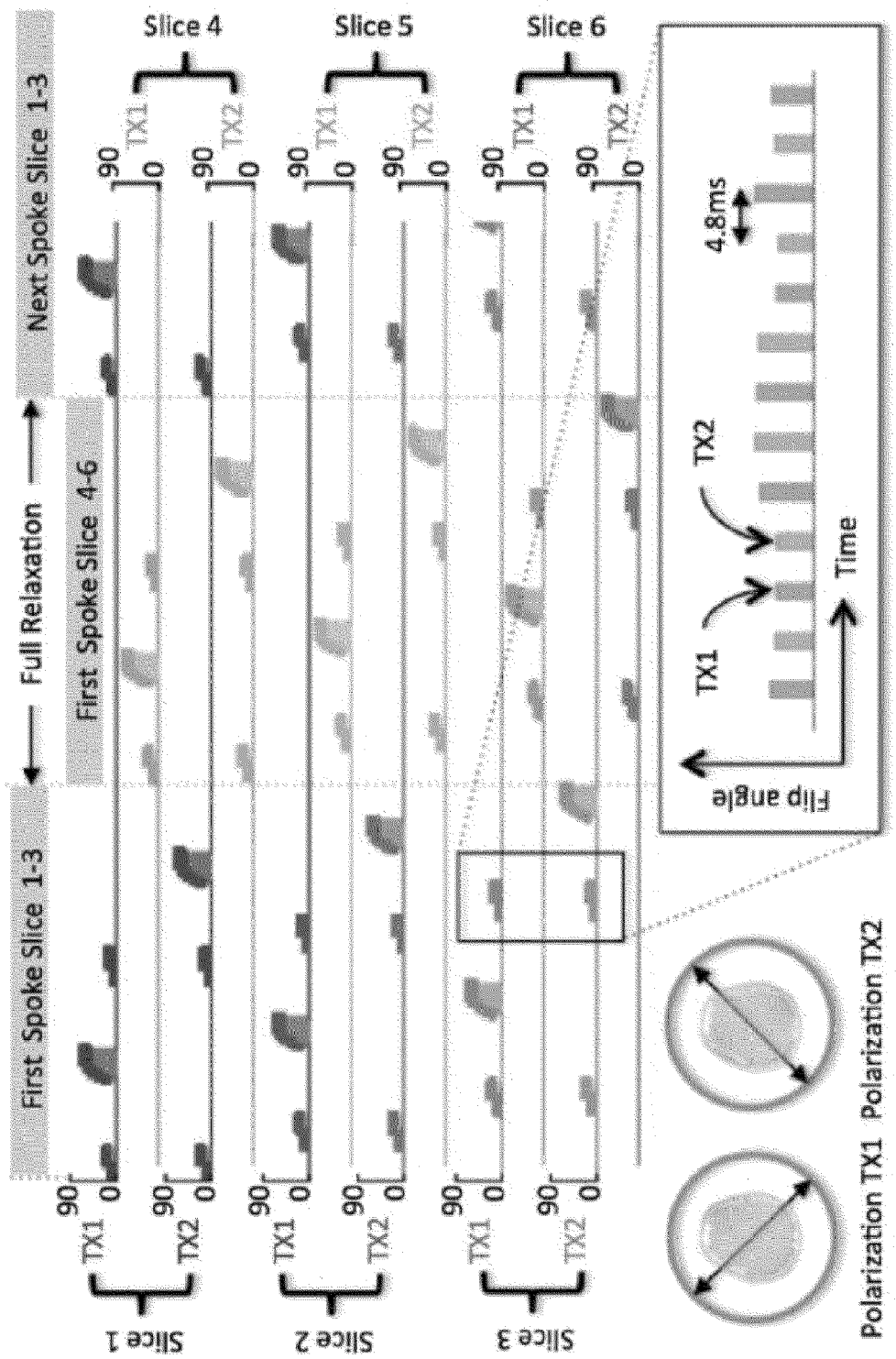
FIG. 12 illustrates a sequence diagram for a plug and play parallel transmit sequence.

To demonstrate this principle, an exemplary generalized PTX fingerprinting sequence was designed, as shown in FIG. 12. FIG. 12 includes 4 segments each containing 120 excitations 4.8 ms apart. The first and third segments include RF spoiled gradient echoes that predominantly encode $B_1^+$ and T1, whereas the other segments also add a T2 relaxation component (without RF spoiling). Collectively, these 480 snapshots capture a distinct signal evolution (corresponding to an MR fingerprint) that simultaneously identifies RF-field distributions and tissue properties. To increase T1 accuracy and help decouple transmit phase interactions, a strategically chosen delay was inserted between segments. Interleaving 6, or more, slices, each delay can be used to image a different slice, thus eliminating all dead time in the protocol. In some instances, a different delay may be advantageous. A golden angle radial sampling strategy was selected to promote incoherence between undersampling artifacts (Cloos et al., 2014, Winkelmann et al. 2007). The reconstruction dictionary was pre-computed based on the extended phase graph formalism (Weigel, 2014) and was permanently stored. The underlying tissue properties in each voxel were retrieved by identifying the dictionary element that best correlates with the compressed fingerprint. The matching algorithm was implemented in MatLab (The MathWorks, Inc., Natick, Mass., United States) augmented with C++ code.

To validate the accuracy of the proposed approach, phantom measurements were performed. The phantom consisted of 7 test tubes (2.5 cm diameter), filled with distilled water doped with different concentrations of Manganese Chloride. The matrix size was 160×160, with an in-plane resolution of 1.5×1.5 $mm^2$, TR/TE=4.8/2.3 ms, 5.0 mm slice thickness. Single spin echo experiments were performed to obtain a gold standard T1 map (TI={25, 50, 100, 200, 400, 800, 1600, 3200, 6400} ms) and T2 map (TE={12, 24, 36, 48, 60, 72, 84, 96, 144, 192, 278, 384} ms). In both cases, a repetition time of 6.5 s was selected to minimize saturation effects. Fitting of the T1 and T2 was performed in Mathematica.

Bilateral leg images from the same subject whose x-ray is illustrated in FIG. 11A were acquired using the lower extremity receive array in a clinical dual-transmit 3 Tesla system (Siemens, Erlangen, Germany). Sequence parameters were: 224×224 matrix, 2×2 $mm^2$ in-plane resolution, TR/TE=4.8/2.3 ms, 5 mm slice. Each snapshot consisted of 22 radial spokes for a total scan time of ~5 min (51 s per slice).

Figure 13:
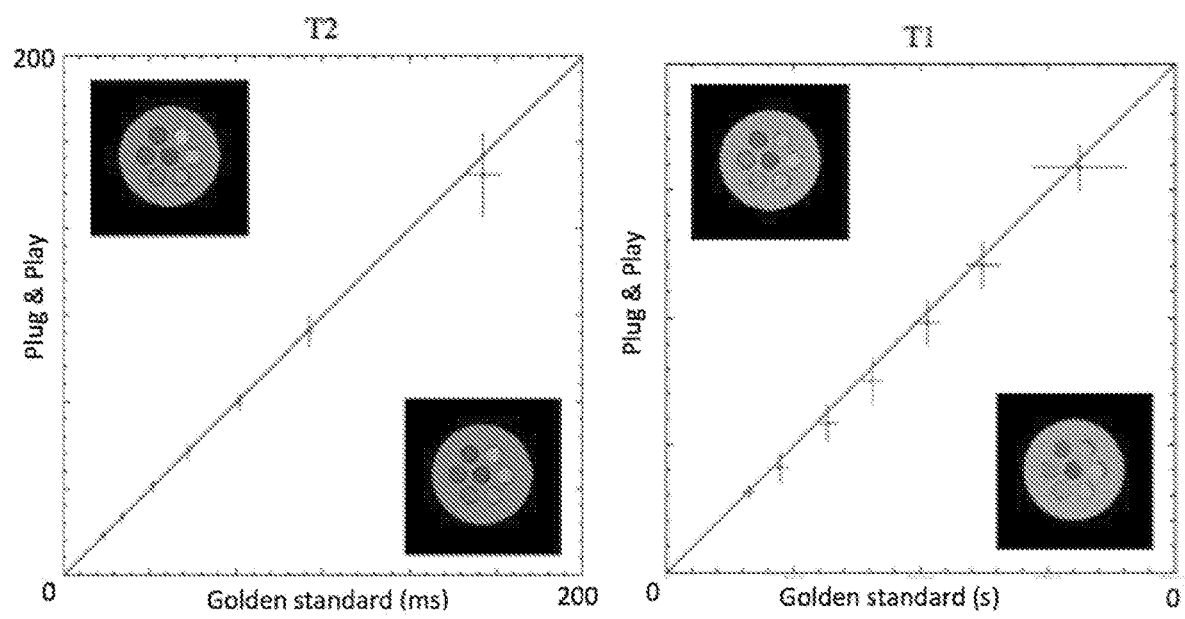
FIG. 13 illustrates a validation of results against established gold standards of T2 (left) and T1 (Right) values obtained with an MR fingerprinting technique according to at least one embodiment.

Results:

Good accuracy and precision were maintained over a broad range of physiological T1 and T2 value, as indicated by the validation against gold standards of T1 and T2 shown in FIG. 13. FIG. 13 includes datapoints indicating the average and standard deviation of T2 and T1 in a different phantom compartment. At the far end of the spectrum, i.e. for T2>150 ms, substantial deviations were observed. Due to the relatedly short duration of the T2 encoding segments (~0.6 s), the encoding of large T2 values may be compromised. If desired, longer segments could be used to increase the sensitivity to long T2.

Figure 14:
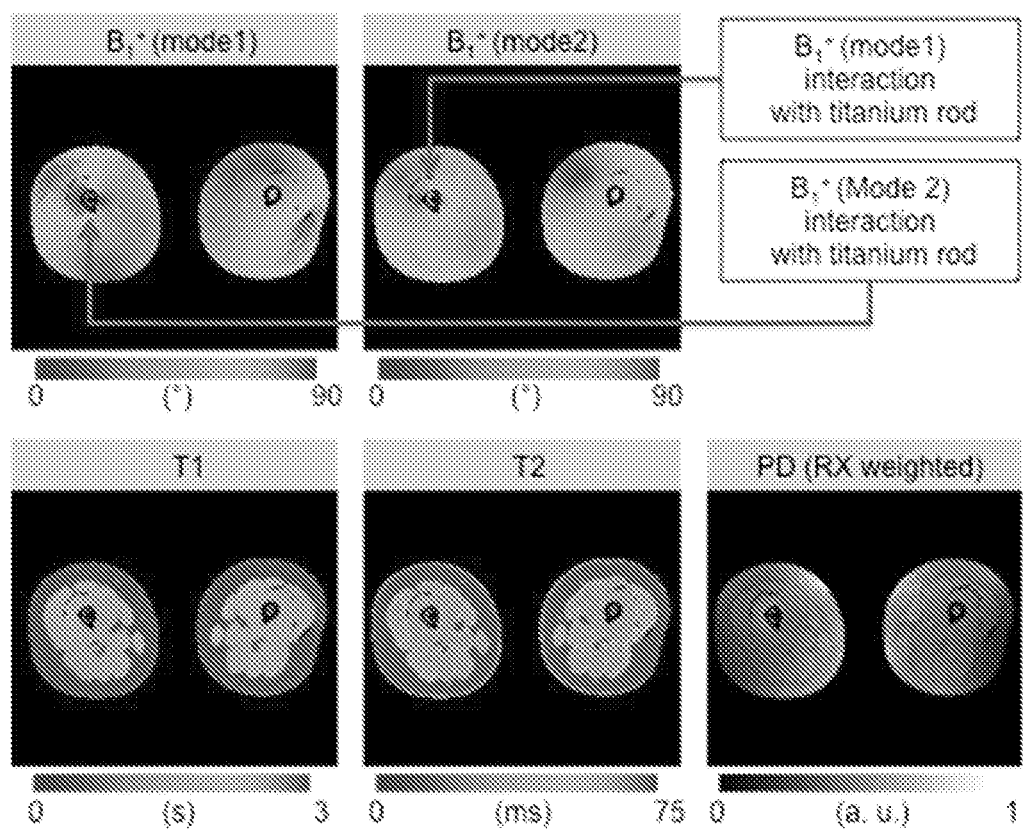
FIG. 14 illustrates: Quantitative parametric maps ($B_1^+$, $B_1^+$, T1, T2) obtained in-vivo at 3 T ($2\times2$ mm$^2$, 5 mm slice, total scan time ~45 s per slice).

The in-vivo measurements revealed RF interactions with the implant, as indicated in the top portion of FIG. 14. Although highly non-uniform, the transmit sensitivities profiles remain complementary, allowing accurate artifact free quantitative maps to be reconstructed throughout the field of view. Further, the lack of adiabatic pulses or other power-intensive pulses in this multi-transmit fingerprinting sequence allowed for low SAR in quantitative imaging (30% of the limit in this study). Moreover, an efficient "plug & play" workflow was maintained, free from patient specific calibrations or complicated procedures. Such an approach may be readily applied for other parts of the body.

Compression

At least some embodiments allow for rapid multi-parametric mapping, in which interweaving multiple transmit-channels into a fingerprinting sequence allows for construction of a parallel transmission framework. Foregoing uniform excitations, such a framework avoids complications arising from certain electrodynamic interactions causing B1+ artifacts in traditional MRI, while maintaining a suitable plug and play workflow. Further, some embodiments provide for fingerprint compression to enable even greater acceleration factors while simultaneously speeding up reconstruction.

Methods:

Fingerprint compression, in at least some embodiments, advantageously may reduce the size of a dictionary by projecting the matching processes from a complex space (phase and amplitude) onto a real space of lower dimension. However, MRF depends on a high degree of incoherence between data samples. Therefore, a compression algorithm which captures the valuable incoherences in the signal is utilized. Additionally, such embodiments accelerate the matching process by reducing the number of data points in each fingerprint. In the context of PTX, such embodiments are particularly advantageous, where the need to resolve the interplay between different transmit phase contributions is a computational burden. In general, each additional transmit-channel adds two more dimensions to the dictionary, which carry little or no information of relevance to everyday clinical imaging. By pairing fingerprint compression with a sequence developed to decouple the transmit-phase interactions, all the phase dimensions (one per transmit channel) may be removed from the dictionary.

A generalized PTX fingerprinting sequence was designed, as shown in FIG. 12, including 4 segments each containing 120 excitations 4.8 ms apart. As mentioned above, the first and third segments contain RF spoiled gradient echoes that predominantly encode B1+ and T1, whereas the other segments also add a T2 relaxation component (without RF spoiling). These 480 snapshots capture a distinct signal evolution (the MR fingerprint) that simultaneously identifies the RF-field distributions and tissue properties. As with certain aforementioned experiments, to increase T1 accuracy and help decouple transmit phase interactions, a strategically chosen delay was inserted between segments. In interleaving at least half a dozen slices, each delay allowed for imaging a different slice, removing dead time. As with certain other experiments, a golden angle radial sampling strategy was selected to promote incoherence between undersampling artifacts.

Figure 15A:
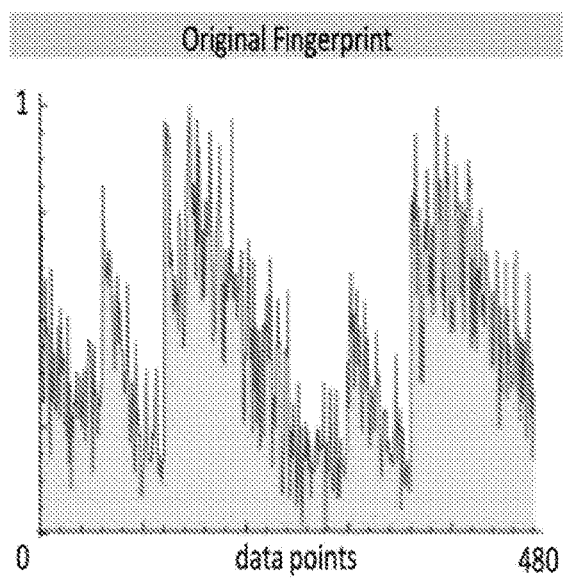
FIG. 15A illustrates a fingerprint before compression according to an embodiment.
Figure 15B:
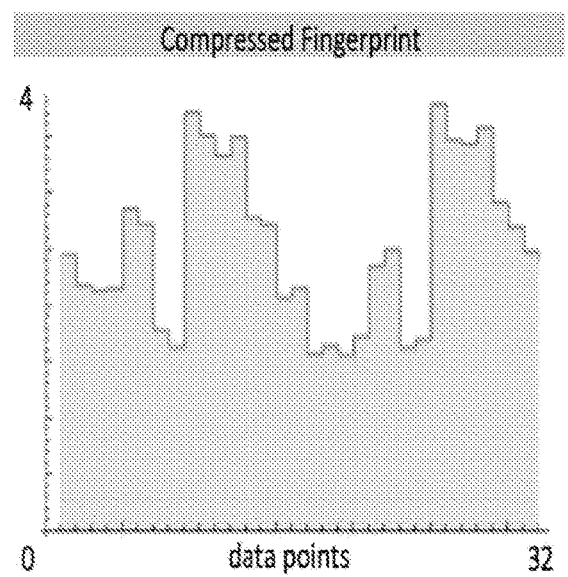
FIG. 15B illustrates a fingerprint after compression according to an embodiment.

FIG. 15A illustrates an example fingerprint before compression. FIG. 15B illustrates an example fingerprint after compression. Effectively, the procedure integrates sets of 15 data points. Based on the sequence design, these subsets were arranged such that all data points had the same underlying transmit phase. During the scan multiple transmit-channels are interleaved, as indicated in the magnified portion of FIG. 12. Because each channel produced a different phase distribution, the compression arranged the subset based on the expected phase configuration defined in the sequence. Prior to summation, the signal contributions from each receiver was multiplied by the conjugate of the receive sensitivity estimated from the k-space center. This way, the incoherent phase contributions due to aliasing artifacts interfere destructively. Under ideal conditions, this would result in a real valued compressed fingerprint. In practice, some phase variations and residual aliasing artifacts may remain. However, these may be disregarded by taking the absolute value. The same compression was applied to the pre-simulated dictionary (Weigel, 2014) and permanently stored. The underlying tissue properties were retrieved by identifying the dictionary element that best correlates with the compressed fingerprint. The matching algorithm was implemented in MatLab (The MathWorks, Inc., Natick, Mass., United States) augmented with C++ code.

Brain images were acquired using a standard 20-channel head-neck receive coil in a clinical dualtransmit 3 Tesla system (Siemens, Erlangen, Germany). Sequence parameters were: 160×160 matrix, 1.5×1.5 mm2 in-plane resolution, 4 mm slice. Three different acceleration factors were used {2, 28, 84} corresponding to {126, 9, 3} radial spokes snapshot and to a total scan time of {290, 21, 7} seconds per slice, as indicated in FIGS. 15A and 15B.

Figure 16:
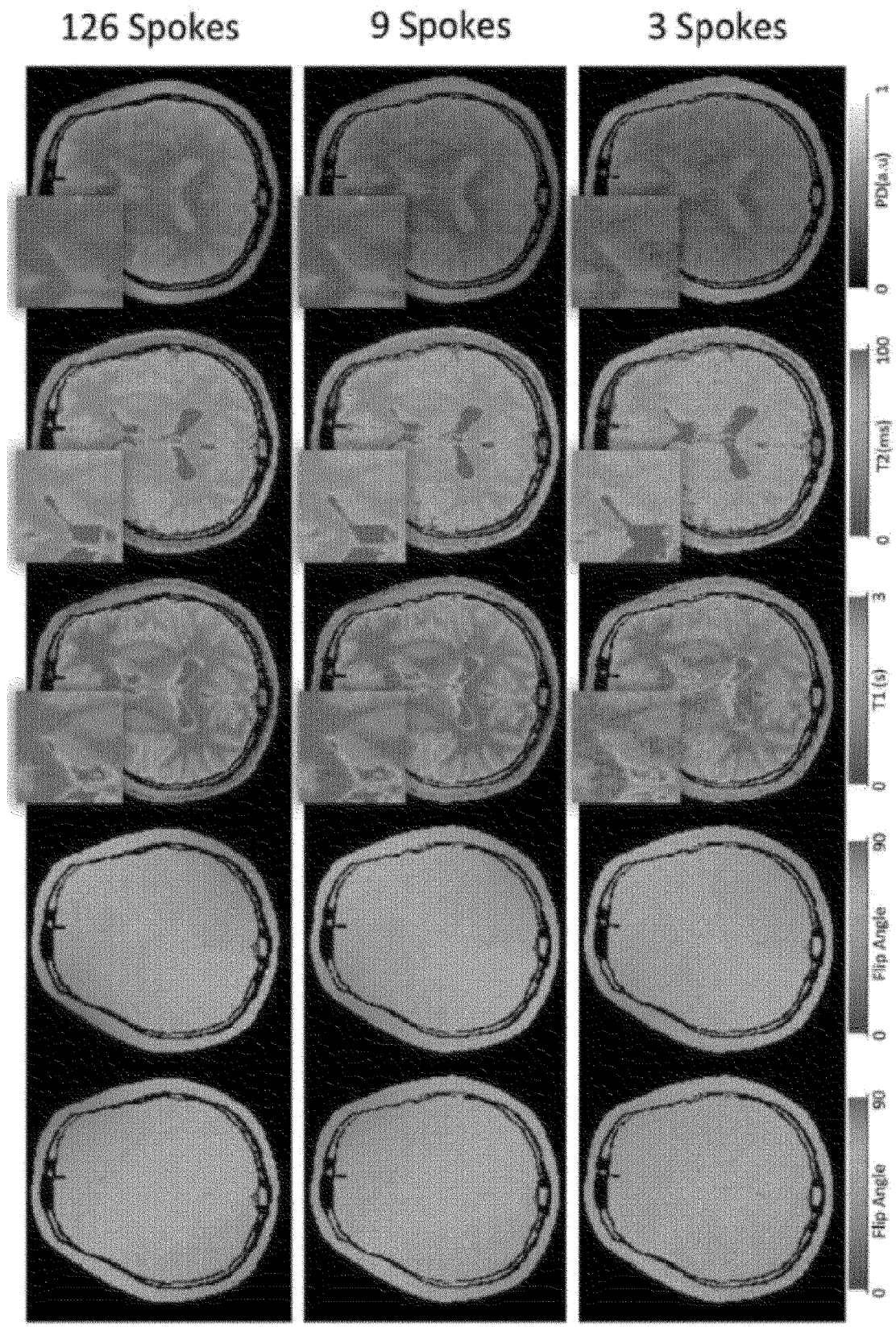
FIG. 16 illustrates parametric maps (B1+, B1+, T1, T2, PD) reconstructed based on a full 480 sample fingerprint.
Figure 17:
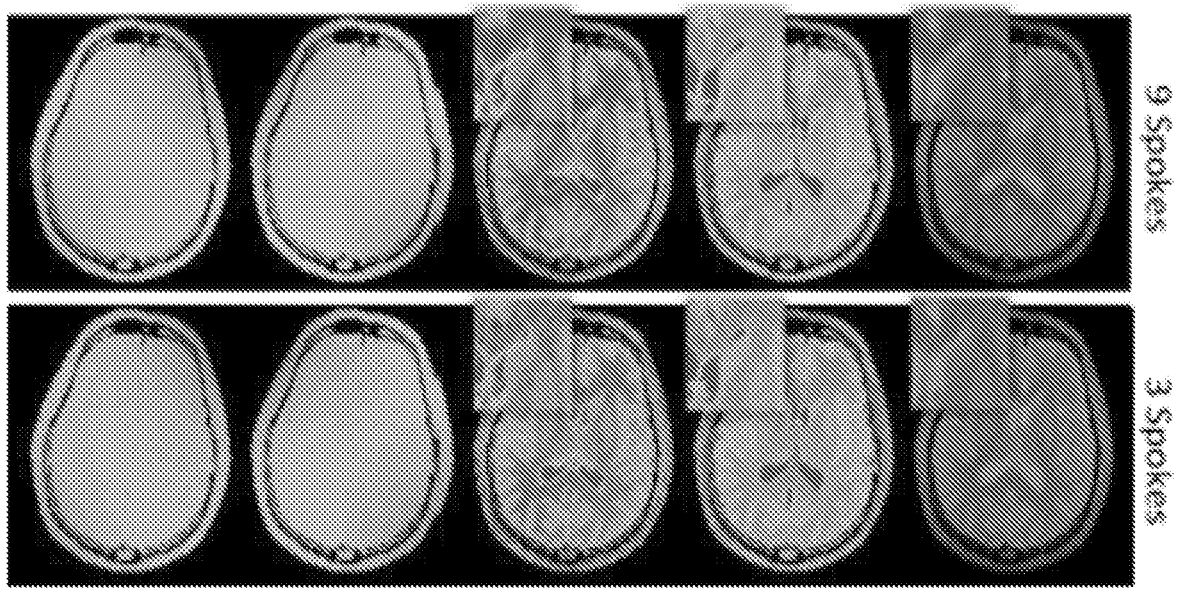
FIG. 17 illustrates parametric maps reconstructed with fingerprint compression according to an embodiment (with the same shading/color scale as FIG. 16).

Results and Discussion:

FIG. 17 illustrates parametric maps reconstructed with fingerprint compression according to an embodiment. The top row of FIG. 17 shows parametric maps reconstructed using the nearly fully sampled data set (126 Spokes). Based on extensive phantom validations, the values were shown to be accurate. The results indicated that as the acceleration factor is increased, the uncompressed reconstruction gradually starts to deviate, as indicated in the center row of FIG. 16. When pushed to an extreme (an acceleration factor of 84), both T1 and T2 values were significantly deteriorated, as indicated in the bottom row of FIG. 16. Using the compression approach of certain embodiments allowed for a high accuracy to be maintained, revealing almost no changes compared to a near full sampling of k-space, as indicated, for example, by the top row of FIG. 17. Even at an acceleration factor of 84, the parametric maps remain comparable to the 'ground truth,' as indicated in the bottom row of FIG. 17. However, when using only 3 spokes per snapshot, noise started to appear in the quantitative maps, suggesting that the SNR became a limiting factor. In addition to enabling a further 3+ fold reduction in scan time, the compression decreased dictionary size from 32 GB to 1 GB and reduced the reconstruction time from nearly an hour to less than one minute per slice. Although the approach of some embodiments is applicable to single transmit systems, it may result in particular benefits in a PTX context.

Conclusion:

MR fingerprint compression allowed for simultaneously quantification of B1+(for 2 transmit channels), T1, T2 and PD, representing additional dimension coverage at a substantially higher resolution (1.5 vs 2.3 mm) in less time (7 vs 12.3 s). Moreover, a simple plug and play PTX workflow may be maintained, which inherently circumvents the detrimental effects of excitation non-uniformities that hamper traditional MRI and MRF experiments.

Computer Implementations

Figure 10:
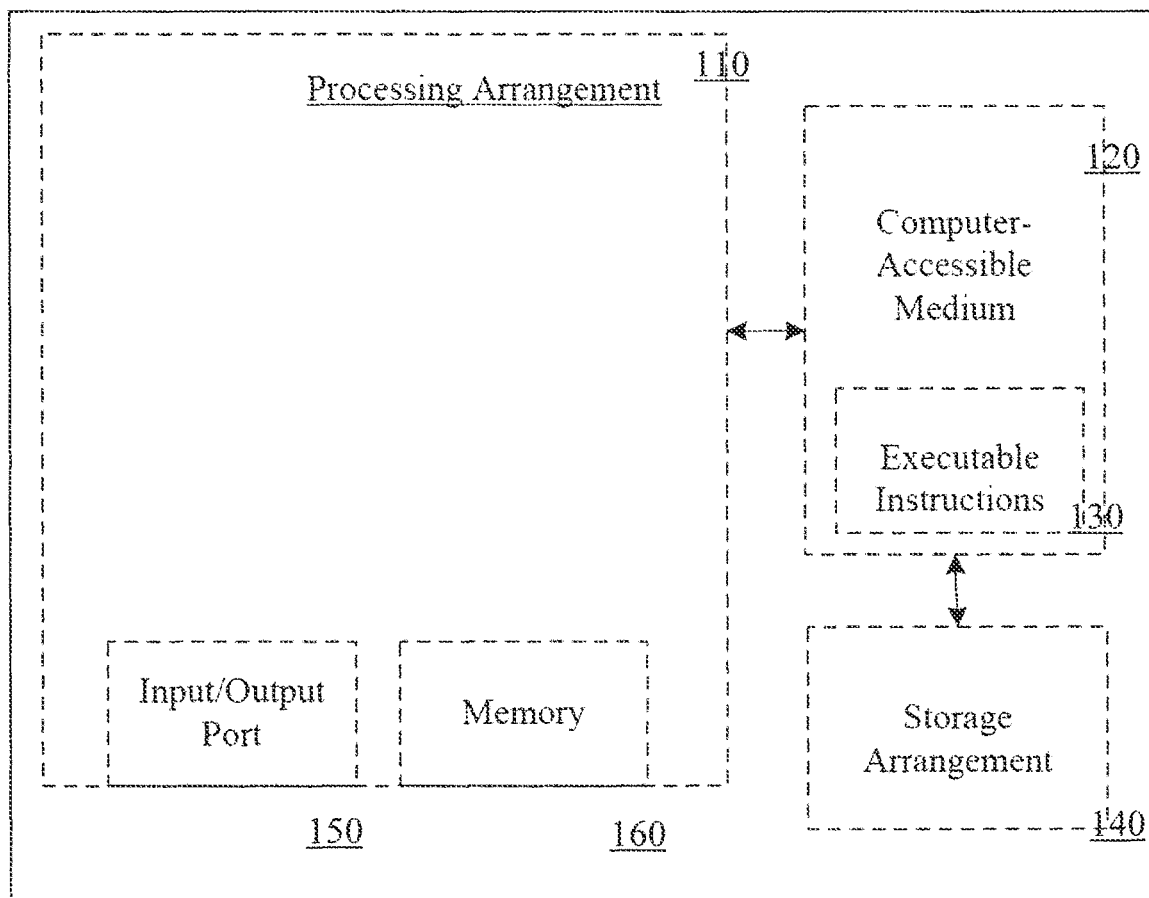
FIG. 10 illustrates one implementation utilizing a computer system.

As shown in FIG. 10, e.g., a computer-accessible medium 120 (e.g., as described herein, a storage device such as a hard disk, floppy disk, memory stick, CD-ROM, RAM, ROM, etc., or a collection thereof) can be provided (e.g., in communication with the processing arrangement 110). The computer-accessible medium 120 may be a non-transitory computer-accessible medium. The computer-accessible medium 120 can contain executable instructions 130 thereon. In addition or alternatively, a storage arrangement 140 can be provided separately from the computer-accessible medium 120, which can provide the instructions to the processing arrangement 110 so as to configure the processing arrangement to execute certain exemplary procedures, processes and methods, as described herein, for example.

System 100 may also include a display or output device, an input device such as a key-board, mouse, touch screen or other input device, and may be connected to additional systems via a logical network. Many of the embodiments described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art can appreciate that such network computing environments can typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Various embodiments are described in the general context of method steps, which may be implemented in one embodiment by a program product including computer-executable instructions, such as program code, executed by computers in networked environments. Generally, program modules include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps.

Software and web implementations of the present invention could be accomplished with standard programming techniques with rule based logic and other logic to accomplish the various database searching steps, correlation steps, comparison steps and decision steps. It should also be noted that the words "component" and "module," as used herein and in the claims, are intended to encompass implementations using one or more lines of software code, and/or hardware implementations, and/or equipment for receiving manual inputs.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A system for whole body magnetic resonance imaging comprising:
    a plurality of radio frequency transmitters in communication with a computer system, each of the plurality of radio frequency transmitters being configured to independently drive a coil element of a plurality of coil elements, wherein each of the plurality of coil elements produces a set of distinct B1+ distributions,
    the computer system comprising a tangible computer-readable medium including computer code configured to
        receive magnetic resonance information including the distinct B1+ distributions produced by the plurality of coil elements, the B1+ distributions being associated with non-uniform transmit sensitivities;
        search a database having an MRI library for a match to the received magnetic resonance information; and
        for every voxel of a plurality of voxels within a volume of interest, search the MRI library for two library elements that best match the magnetic resonance information.

2. The system of claim 1, wherein each of the plurality of coil elements are positioned relative to each other and the volume of interest, whereby every voxel within the volume of interest is exposed to electromagnetic energy from at least one of the plurality of coil elements.

3. The system of claim 1, wherein the plurality of coil elements are configured for parallel transmission.

4. The system of claim 1, wherein the plurality of coil elements are configured to generate a greater than 7 Tesla magnetic field.

5. The system of claim 1, wherein the plurality of coil elements include groups of coil elements.

6. The system of claim 1, wherein the MM library contains information obtained via simulation of non-linear Bloch equations.

7. A nontransitory computer-readable memory having instructions thereon, the instructions comprising:
  instructions for transmitting a radio frequency signal from a plurality of coil elements to a volume of interest, where each of the plurality of coil elements transmits an independent radio frequency signal producing a distinct B1+ distribution, the B1+ distributions being associated with non-uniform transmit sensitivities;
  instructions for receiving induced radio frequency signals from a material in the volume of interest;
  instructions for identifying the material based upon perform matching utilizing magnetic resonance information including the distinct B1+ distribution associated with each of the plurality of coil elements,
  instructions for searching a database having an MM library for a match to the received magnetic resonance information; and
  instructions for, for every voxel of a plurality of voxels within the volume of interest, searching the MRI library for two library elements that best match the magnetic resonance information.

8. The nontransitory computer-readable memory of claim 7, further including instructions for interleaving transmit sensitivities associated with each of the plurality of coil elements.

9. The nontransitory computer-readable memory of claim 7, further comprising instructions for defining the volume of interest whereby every voxel within the volume of interest is exposed to electromagnetic energy from at least one of the plurality of coil elements.

10. A method for identifying a material, comprising:
  transmitting a radio frequency signal from a plurality of coil elements to a volume of interest, where each of the plurality of coil elements transmits an independent radio frequency signal producing a distinct B1+ distribution, the B1+ distributions being associated with non-uniform transmit sensitivities;
  receiving induced radio frequency signals from a material in the volume of interest; and
  identifying the material based upon performing matching utilizing magnetic resonance information including the distinct B1+ distribution associated with each of the plurality of coil elements,
  wherein the matching comprises searching a database having an MRI library for a match to the received magnetic resonance information; and
  for every voxel of a plurality of voxels within the volume of interest, searching the MRI library for two library elements that best match the magnetic resonance information.

11. The method of claim 10 further including interleaving transmit sensitivities associated with each of the plurality of coil elements.

12. The method of claim 11, further comprising compressing the interleaved transmit sensitivities.

13. The method of claim 11, further comprising determining a delay and providing for at least one delay during the receiving of the induced radio frequency signals from the material.

14. The method of claim 10, further comprising defining a volume of interest, whereby every voxel within the volume of interest is exposed to electromagnetic energy from at least one of the plurality of coil elements.

15. The method of claim 10, further comprising inducing a greater than 7 Tesla magnetic field.

16. A system for magnetic resonance fingerprinting in the presence of strong B1+(r) non-uniformities comprising:
  a processor; and
  a tangible computer-readable medium operatively connected to the processor and including computer code configured to:
    receive magnetic resonance information regarding a material including B1+ information, the B1+ information being associated with non-uniform transmit sensitivities;
    search a database having an MRI library for a match to the received magnetic resonance information;
    for every voxel of the plurality of voxels, searching the MRI library for two library elements that best match the magnetic resonance information, and
    identify the material based upon the best match.

17. The system of claim 16, further comprising computer code configured for limiting the searching of the MRI library based on premeasured B1+ information.

18. The system of claim 16, wherein the magnetic resonance information corresponds to a plurality of voxels.

19. The system of claim 16, further comprising computer code configured to search the MM library for elements matching compressed MM resonance information.

20. The system of claim 16, further comprising computer code configured to insert at least one delay during the receiving of the magnetic resonance information regarding the material.

* * * * *